United States Patent
Hiraoka et al.

(10) Patent No.: US 10,149,604 B2
(45) Date of Patent: Dec. 11, 2018

(54) ENDOSCOPE HAVING A BIOPSY NEEDLE WITH NEEDLE ELEVATION MECHANISM

(71) Applicant: OLYMPUS CORPORATION, Tokyo (JP)

(72) Inventors: Jin Hiraoka, Sagamihara (JP); Hiroshi Kodama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/832,049

(22) Filed: Dec. 5, 2017

(65) Prior Publication Data

US 2018/0092512 A1    Apr. 5, 2018

Related U.S. Application Data

(63) Continuation of application No. PCT/JP2016/066595, filed on Jun. 3, 2016.

(30) Foreign Application Priority Data

Jun. 10, 2015   (JP) .................................. 2015-117855

(51) Int. Cl.
  *A61B 8/12*   (2006.01)
  *A61B 1/00*   (2006.01)
  *A61B 1/018*   (2006.01)
(52) U.S. Cl.
  CPC ............ *A61B 1/00098* (2013.01); *A61B 1/00* (2013.01); *A61B 1/018* (2013.01); *A61B 8/12* (2013.01)
(58) Field of Classification Search
  CPC ................................................ A61B 1/00098
  See application file for complete search history.

(56) References Cited

U.S. PATENT DOCUMENTS 5,730,701 A    3/1998 Furukawa et al.
2002/0193741 A1*  12/2002 Secrest .............. A61B 1/00098
                                                          604/164.06
(Continued)

FOREIGN PATENT DOCUMENTS

JP    H09-075296 A    3/1997
JP    H11-4804 A    1/1999
(Continued)

OTHER PUBLICATIONS

JP2007330756 Endoscope with English Translation.*
(Continued)

*Primary Examiner* — Serkan Akar
(74) *Attorney, Agent, or Firm* — Scully, Scott, Murphy & Presser, P.C.

(57) ABSTRACT

An endoscope includes an insertion portion, the endoscope being configured to allow a treatment tool to protrude from the insertion portion. The endoscope further includes: a treatment tool elevator base configured to be elevated by rotation around a rotation shaft with respect to a direction in which the insertion portion extends; an operating portion configured to input operation of changing an angle of elevating the treatment tool with respect to the treatment tool elevator base; a wire configured to be connected to the operating portion; a first member including a first engagement portion; and a second member including a second engagement portion and a wire connection portion to be connected to the wire, the second member being configured to: be supported so as to be rotatable with respect to the rotation shaft; and transmit the operation to the treatment tool elevator base.

6 Claims, 16 Drawing Sheets

(56) References Cited

U.S. PATENT DOCUMENTS

| | | | |
|---|---|---|---|
| 2005/0228289 A1* | 10/2005 | Kohno | A61B 1/00098 |
| | | | 600/463 |
| 2007/0265494 A1 | 11/2007 | Leanna et al. | |
| 2009/0182194 A1 | 7/2009 | Wood et al. | |
| 2015/0031947 A1 | 1/2015 | Kudo et al. | |

FOREIGN PATENT DOCUMENTS

| | | | | |
|---|---|---|---|---|
| JP | 2007-215634 A | | 8/2007 | |
| JP | 2007330756 A | * | 12/2007 | ......... A61B 1/00098 |
| WO | WO 2014136326 A1 | | 9/2014 | |

OTHER PUBLICATIONS

International Search Report dated Jul. 5, 2016 issued in PCT/JP2016/066595.

Japanese Decision to Grant a Patent dated Apr. 4, 2017 issued in JP 2017-513574.

\* cited by examiner

ENDOSCOPE HAVING A BIOPSY NEEDLE WITH NEEDLE ELEVATION MECHANISM

CROSS-REFERENCE TO RELATED APPLICATIONS

This application is a continuation of PCT international application Ser. No. PCT/JP2016/066595 filed on Jun. 3, 2016 which designates the United States, incorporated herein by reference, and which claims the benefit of priority from Japanese Patent Application No. 2015-117855, filed on Jun. 10, 2015, incorporated herein by reference.

BACKGROUND

1. Technical Field

The disclosure relates to an endoscope.

2. Related Art

There is a known endoscope inserted into a subject for examination of a site to be examined. This type of endoscope is widely used in a medical field, or the like. Some of recent endoscopes include a treatment tool elevator base for directing a treatment tool such as a puncture needle for performing treatment inside the subject, to an affected site. For example, JP 2007-215634 A discloses a treatment tool elevator base rotatably supported by a rotation shaft. In this technique, the treatment tool elevator base is rotated by pulling an operation wire connected to the treatment tool elevator base toward a proximal end side, thereby elevating the treatment tool.

SUMMARY

In some embodiments, an endoscope includes an insertion portion to be inserted into a subject, the endoscope being configured to allow a treatment tool to protrude from a distal end of the insertion portion. The endoscope further includes: a treatment tool elevator base configured to be supported by a rotation shaft arranged at a distal end portion of the insertion portion and to be elevated by rotation around the rotation shaft with respect to a direction in which the insertion portion extends; an operating portion configured to be arranged on a proximal end side of the insertion portion and to input operation of changing an angle of elevating the treatment tool with respect to the treatment tool elevator base; a wire configured to be connected to the operating portion and to be arranged along the direction in which the insertion portion extends; a first member including a first engagement portion and being formed integrally with the rotation shaft; and a second member including a second engagement portion configured to be engaged with the first engagement portion of the first member and a wire connection portion to be connected to the wire, the second member being configured to: be supported so as to be rotatable with respect to the rotation shaft; and transmit the operation to the treatment tool elevator base. The wire connection portion is positioned on a side opposite to an elevation side on which the treatment tool is elevated with respect to a reference plane including the direction in which the insertion portion extends and a direction along an axis of the rotation shaft.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
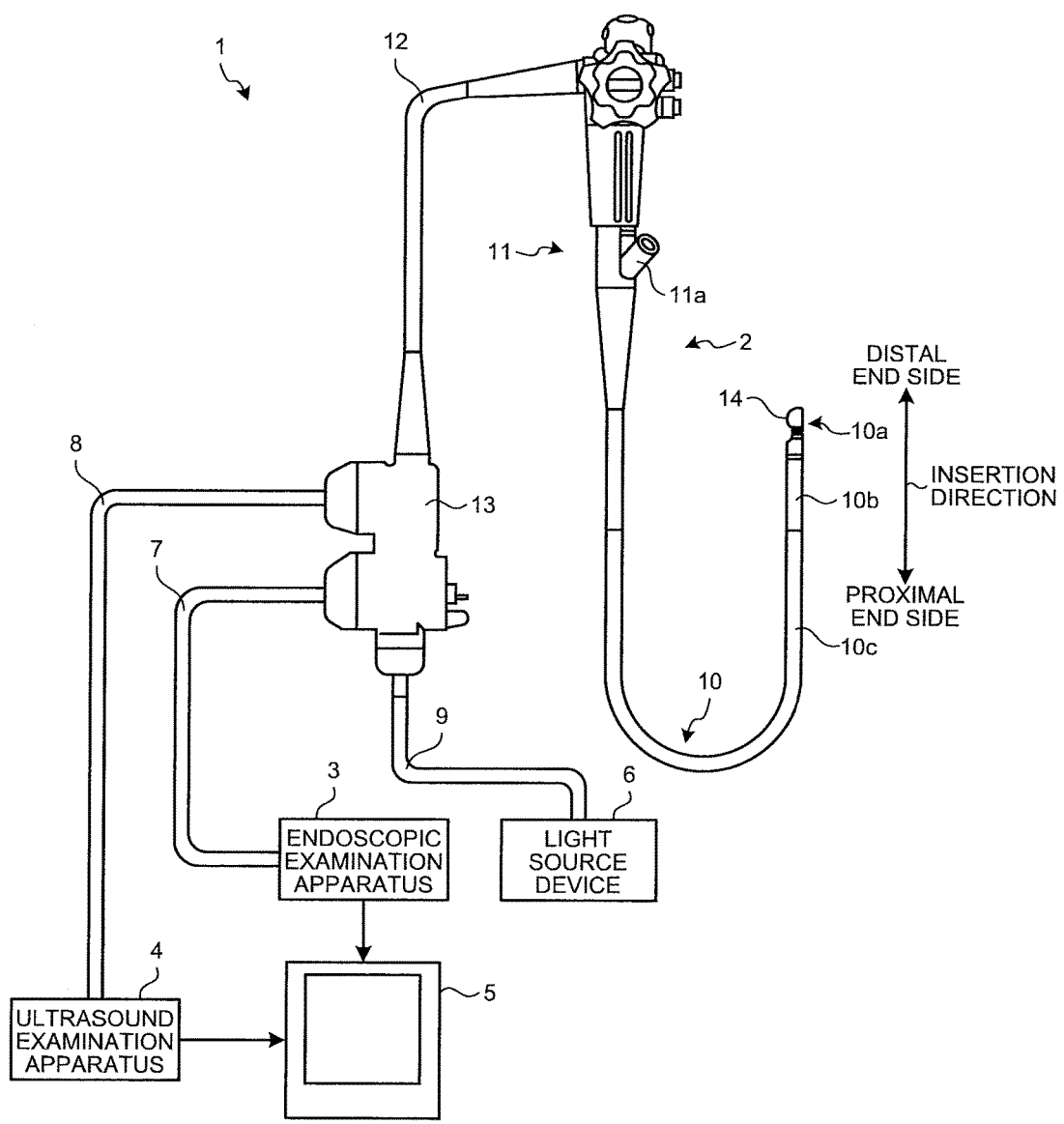
FIG. 1 is a schematic diagram illustrating a configuration of an ultrasound diagnosis system including an ultrasound endoscope according to a first embodiment of the disclosure.

Hereinafter, embodiments of an endoscope according to the disclosure will be described with reference to the drawings. Note that the disclosure is not limited by these embodiments. While an ultrasound endoscope having an ultrasound transducer for examining an examination object with ultrasound will be described as an example in the following embodiments, the disclosure can be generally applied to an endoscope using a treatment tool such as a puncture needle used for performing treatment inside the subject.

In the description of the drawings, the same reference numerals are given to same portions or corresponding portions. Moreover, the drawings are schematic, and it should be taken into consideration that a relation between sizes of elements or the like may be different from an actual one. A mutual relation in size or ratio may be different between the drawings.

First Embodiment

FIG. 1 is a schematic diagram illustrating a configuration of an ultrasound diagnosis system including an ultrasound endoscope according to a first embodiment of the disclosure. An ultrasound diagnosis system 1 illustrated in FIG. 1 includes an ultrasound endoscope 2, an endoscopic examination apparatus 3, an ultrasound examination apparatus 4, a display device 5, a light source device 6, a video cable 7, an ultrasound cable 8, and a light source cable 9. The video cable 7 connects the ultrasound endoscope 2 with the endoscopic examination apparatus 3. The ultrasound cable 8 connects the ultrasound endoscope 2 with the ultrasound examination apparatus 4. The light source cable 9 connects the ultrasound endoscope 2 with the light source device 6.

The ultrasound endoscope 2 includes an examination optical system and an ultrasound transducer and has an endoscopic examination function and an ultrasound examination function. The examination optical system includes a lens and an imaging element as an examination unit for examining the examination target and examines an optical image of the examination target by capturing the image. The ultrasound transducer includes an ultrasound transceiver and examines the examination target with ultrasound. The endoscopic examination apparatus 3 controls the endoscopic examination function and processes an output signal output from the ultrasound endoscope 2 by endoscopic examination. The ultrasound examination apparatus 4 controls the ultrasound examination function and processes the output signal output from the ultrasound endoscope 2 by ultrasound examination. The display device 5 obtains an output signal output from the endoscopic examination apparatus 3 and the ultrasound examination apparatus 4, for example, and appropriately displays at least one of an endoscope image and an ultrasound tomographic image. The light source device 6 includes a light source for supplying illumination light for performing endoscopic examination.

The ultrasound endoscope 2 includes an insertion portion 10, an operating portion 11, a universal cord 12, and a connector portion 13. The insertion portion 10 includes an examination unit at its distal end and is inserted into the subject. The operating portion 11 is continuous with a proximal end side of the insertion portion 10. The universal cord 12 extends from a side portion of the operating portion 11. The connector portion 13 is continuous with the universal cord 12 and connected to each of the video cable 7, the ultrasound cable 8, and the light source cable 9. In this specification, as illustrated in FIG. 1, the direction in which the insertion portion 10 extends is referred to as the "insertion direction", and the "distal end side" and "proximal end side" described below are directions indicated by arrows illustrated in each of the diagrams.

The insertion portion 10 includes, in an order from the distal end side, a distal end portion 10a, a bending portion 10b, and a flexible tube portion 10c. The bending portion 10b is formed to be bendable according to the operation of the operating portion 11. The flexible tube portion 10c has flexibility. The proximal end of the flexible tube portion 10c is continuous with the distal end side of the operating portion 11. An ultrasound transducer 14 is arranged on the distal end side of the distal end portion 10a. Furthermore, a treatment tool elevating base for elevating the distal end of a treatment tool described below is arranged at the distal end portion 10a.

The operating portion 11 includes a treatment tool insertion port 11a for introducing a puncture needle, or the like, as a treatment tool, into the subject. A treatment tool insertion passage is provided inside the insertion portion 10, and the treatment tool insertion port 11a serves as an insertion port of the treatment tool insertion passage. Moreover, by operating the operating portion 11, it is possible to input operation of changing an angle of elevating the treatment tool with respect to the treatment tool elevator base, to be described below.

The ultrasound endoscope 2 and the endoscopic examination apparatus 3 are electrically connected with each other via the video cable 7 connected to the connector portion 13. The ultrasound endoscope 2 and the ultrasound examination apparatus 4 are electrically connected with each other via the ultrasound cable 8 connected to the connector portion 13. The light source cable 9 is an optical fiber cable. The ultrasound endoscope 2 and the light source device 6 guide the illumination light from the light source of the light source device 6, to the ultrasound endoscope 2 using the light source cable 9 connected to the connector portion 13.

Figure 2:
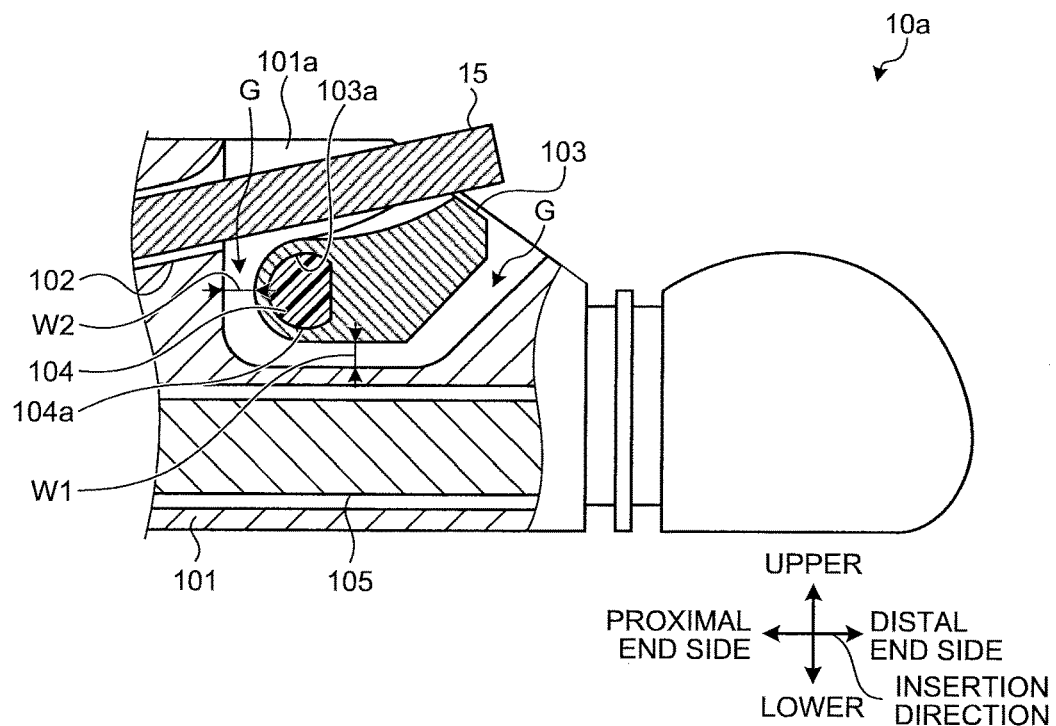
FIG. 2 is a schematic diagram of a distal end portion of the ultrasound endoscope illustrated in FIG. 1.
Figure 3:
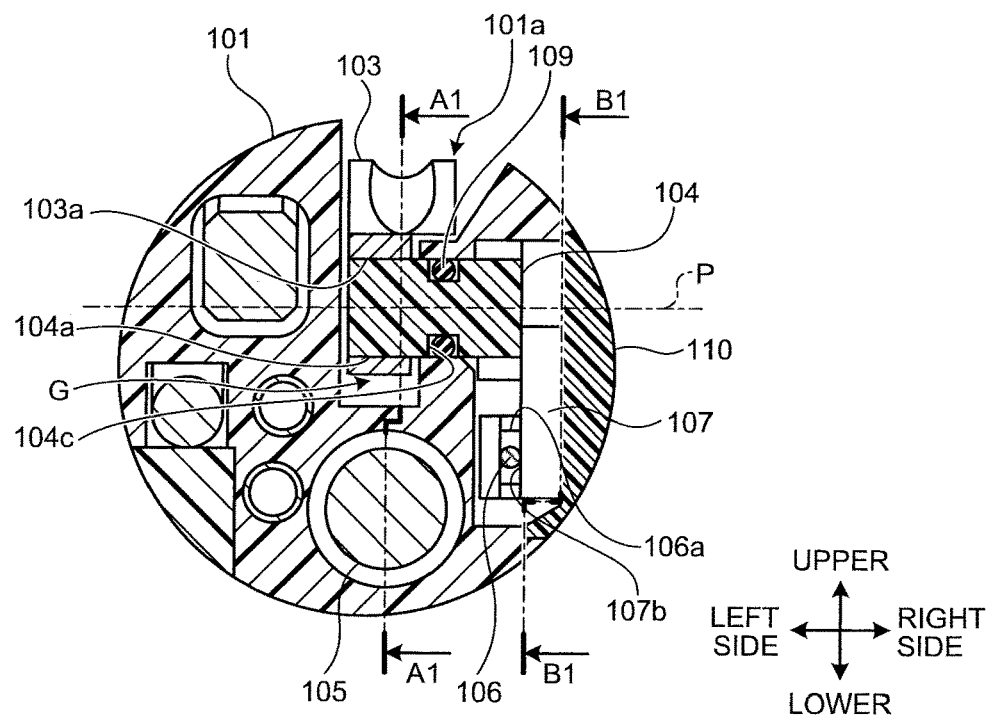
FIG. 3 is a schematic diagram of a surface orthogonal to an insertion direction of the distal end portion of the ultrasound endoscope illustrated in FIG. 1.
Figure 4:
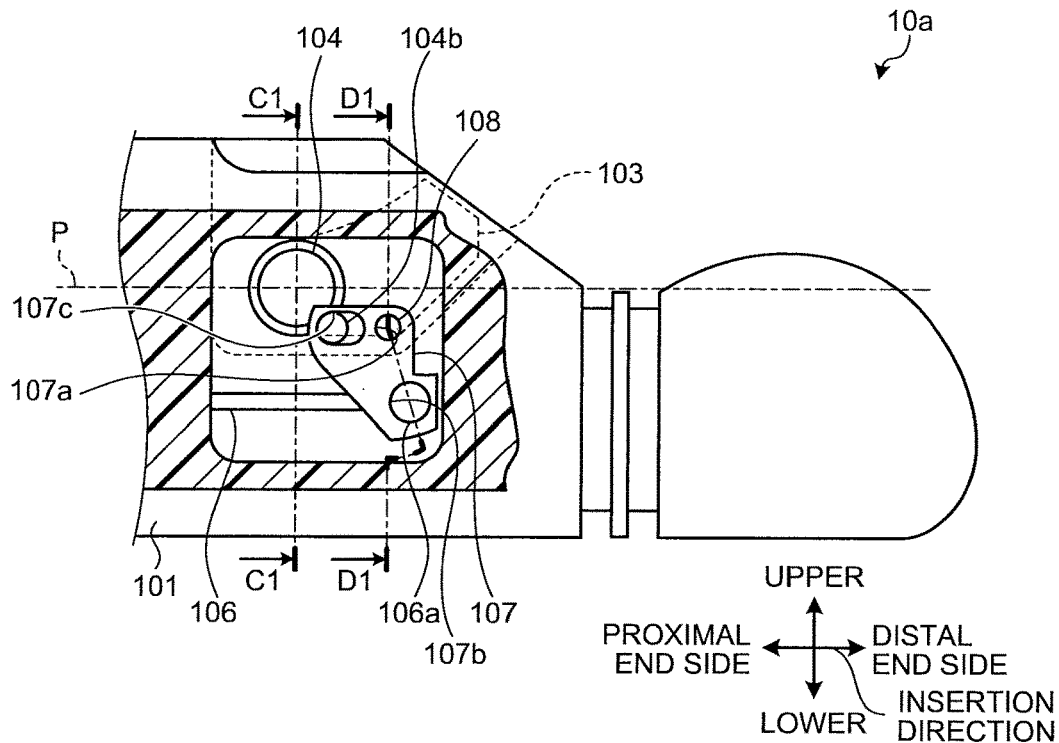
FIG. 4 is a partial cross-sectional view of a cross section taken along line B1-B1 in FIG. 3, viewed from the right side.
Figure 5:
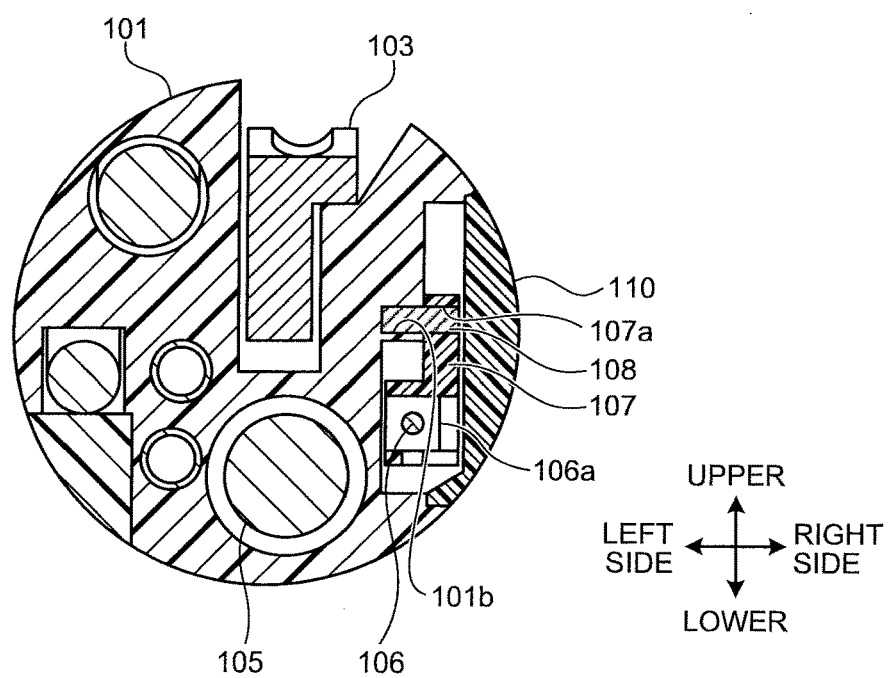
FIG. 5 is a cross-sectional view of the cross section taken along line D1-D1 in FIG. 4, viewed from the proximal end side.

FIG. 2 is a schematic diagram of a distal end portion of the ultrasound endoscope illustrated in FIG. 1. FIG. 3 is a schematic diagram of a surface orthogonal to an insertion direction of the distal end portion of the ultrasound endoscope illustrated in FIG. 1. FIG. 2 is a partial cross-sectional view of the cross section taken along line A1-A1 in FIG. 3, viewed from the right side. FIG. 4 is a partial cross-sectional view of a cross section taken along line B1-B1 in FIG. 3, viewed from the right side. FIG. 3 is a cross-sectional view of the cross section taken along line C1-C1 in FIG. 4, viewed from the proximal end side. FIG. 5 is a cross-sectional view of the cross section taken along line D1-D1 in FIG. 4, viewed from the proximal end side. In the present specification, "upper", "lower", "right side", and "left side" described below represent directions indicated by arrows in each of the diagrams.

As illustrated in FIG. 2, the distal end portion 10a includes a distal end rigid portion 101, a treatment tool channel 102, a treatment tool elevator base 103, a first link 104, and a cable 105. The distal end rigid portion 101 is formed of a rigid member. The treatment tool channel 102 is provided for allowing a treatment tool 15 to protrude from the opening of the distal end rigid portion 101. The treatment tool elevator base 103 elevates the treatment tool 15 that protrudes from the treatment tool channel 102. The first link 104 as a first member rotatably supports the treatment tool elevator base 103. The cable 105 extends at a lower portion of the treatment tool elevator base 103 in an insertion direction and is connected to the ultrasound transducer 14. Moreover, as illustrated in FIG. 4, the distal end portion 10a includes a wire 106, a second link 107, and a rotation shaft 108. The wire 106 is arranged along the insertion direction and transmits the operation input into the operating portion 11 to the distal end portion 10a. The second link 107 as a second member transmits the operation from the wire 106 to the first link 104. The rotation shaft 108 rotatably supports the second link 107. Moreover, as illustrated in FIG. 3, the distal end portion 10a includes an O-ring 109 and a cover 110. The O-ring 109 maintains a portion between the distal end rigid portion 101 and the first link 104 watertight. The cover 110 seals each of portions watertight.

Figure 6:
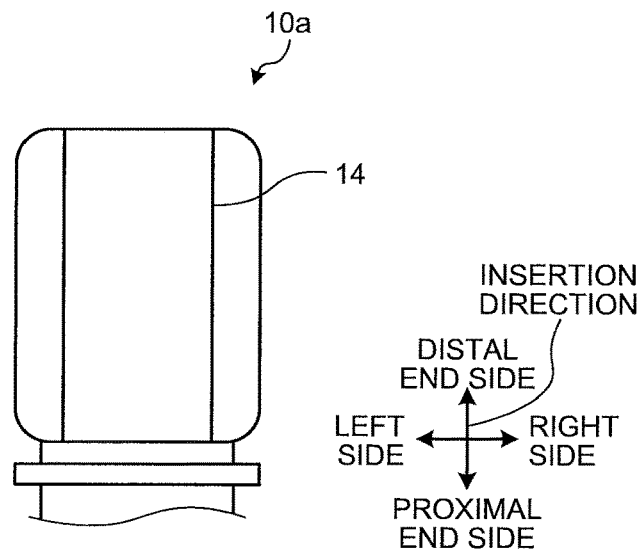
FIG. 6 is a top view of a distal end of the distal end portion illustrated in FIG. 2.

FIG. 6 is a top view of a distal end of the distal end portion illustrated in FIG. 2. The distal end portion 10a includes the ultrasound transducer 14 held by the distal end rigid portion 101. The ultrasound transducer 14 transmits ultrasound and receives ultrasound (ultrasound echo) reflected on the examination target. The ultrasound transducer 14 is a convex ultrasound transducer.

The distal end rigid portion 101 is formed of a rigid member such as resin. As illustrated in FIG. 3, the distal end rigid portion 101 includes an opening 101a for accommodating the treatment tool elevator base 103 in an initial state before elevating the treatment tool 15. A cross section of the opening 101a, which is a cross section orthogonal to the insertion direction, has a tapered shape with the opening width of the opening 101a increasing in the direction (upper direction in FIG. 3) of elevating the treatment tool 15. As illustrated in FIG. 5, a shaft hole 101b is formed in the distal end rigid portion 101.

The treatment tool channel 102 allows the treatment tool 15 inserted from the treatment tool insertion port 11a of the operating portion 11 to protrude from the opening of the distal end rigid portion 101.

As illustrated in FIGS. 2 and 3, a shaft hole 103a is formed in the treatment tool elevator base 103. The treatment tool elevator base 103 is rotatably supported by the first link 104 by fastening a rotation shaft 104a of the first link 104 to the shaft hole 103a with adhesion or a screw. Then, the treatment tool elevator base 103 changes the angle of elevating the treatment tool 15 with respect to the insertion direction, by rotation around the rotation shaft 104a. Moreover, a gap G is provided between the treatment tool elevator base 103 and the distal end rigid portion 101. Each of a width W1 of the gap G in the upper-lower direction and a width W2 of the gap G in the left-right direction in FIG. 2 is 0.5 mm or more and 2 mm or less, for example.

The first link 104 includes the rotation shaft 104a, and an engagement portion 104b as a first engagement portion to be engaged with the second link 107 as illustrated in FIG. 4. Moreover, the first link 104 includes a groove 104c into which the O-ring 109 is fitted, as illustrated in FIG. 3.

The cable 105 electrically connects the ultrasound transducer 14 with the ultrasound examination apparatus 4 via the universal cord 12 and the ultrasound cable 8.

The wire 106 is connected on its proximal end side, with the operating portion 11, and is movable in the insertion direction by operation of the operating portion 11. As illustrated in FIGS. 4 and 5, a distal end portion 106a of the wire 106 has a cylindrical shape extending in the left-right direction in FIG. 5, and is engaged with a wire connection portion 107b (refer to FIGS. 3 and 4) of the second link 107. Moreover, when a plane including the insertion direction and the direction along the axis of the rotation shaft 104a is defined as a reference plane P (refer to FIGS. 3 and 4), the wire 106 is connected to a side (lower direction in FIG. 3) opposite to the elevation side on which the treatment tool 15 is elevated (upper direction in FIG. 3) with respect to the reference plane P.

The second link 107 includes a shaft hole 107a through which the rotation shaft 108 is inserted, and is rotatably supported with respect to the rotation shaft 108. Moreover, as illustrated in FIGS. 3 and 4, the second link 107 includes the wire connection portion 107b. The wire connection portion 107b slidably supports the distal end portion 106a of the wire 106 by being fitted with a cylindrical portion formed at the distal end portion 106a of the wire 106. Furthermore, as illustrated in FIG. 4, a long hole 107c as a second engagement portion is formed in the second link 107. The long hole 107c is engaged with the engagement portion 104b of the first link 104, thereby transmitting the operation from the wire 106 to the first link 104.

Moreover, as illustrated in FIG. 4, the second link 107 has an angle formed between a line connecting the shaft hole 107a with the wire connection portion 107b and a line connecting the shaft hole 107a with the long hole 107c. Therefore, it is possible to sufficiently increase the distance between the shaft hole 107a and the wire connection portion 107b and the distance between the shaft hole 107a and the long hole 107c without enlarging the distal end portion 10a. As a result, it is possible to reduce the force required for the input operation to the wire 106 to elevate the treatment tool 15.

Note that the first link 104 and the second link 107 function as an operation transmission mechanism for transmitting the operation input from the wire 106. The operation transmission mechanism converts the direction of transmitting the operation input from the wire 106 and transmits the operation such that the rotation shaft 104a rotates in a direction of elevating the treatment tool 15.

As illustrated in FIG. 5, one end of the rotation shaft 108 is fixed to the shaft hole 101b of the distal end rigid portion 101 by adhesion, or the like, while the other end is inserted into the shaft hole 107a of the second link 107, whereby the rotation shaft 108 rotatably supports the second link 107.

As illustrated in FIG. 3, the O-ring 109 is formed of an elastic member and fitted into the groove 104c of the first link 104 to maintain a portion between the distal end rigid portion 101 and the first link 104 watertight. The cover 110 has a shape slightly larger than the opening of the distal end rigid portion 101 and is fixed to the distal end rigid portion 101 by adhesion, or the like. Additionally, the O-ring 109 and the cover 110 maintain watertightness in a region including the engagement portion 104b, the wire 106, and the second link 107 from the right side of the groove 104c of the first link 104 in FIG. 3. As a result of this arrangement, these watertight regions are regions to which no dirt adheres at the use of the ultrasound endoscope 2, and thus, regions for which no cleaning is needed.

Next, operation of rotating the treatment tool elevator base 103 of the ultrasound endoscope 2 from the initial state to the elevated state will be described. First, when the wire 106 is pulled to the proximal end side by the operation of the operating portion 11 in the initial state of FIG. 4, the second link 107 rotates clockwise in FIG. 4 around the rotation shaft 108 as an axis in conjunction with the wire 106. When the second link 107 rotates, the long hole 107c of the second link 107 is engaged with the engagement portion 104b of the first link 104, thereby rotating the first link 104 counterclockwise in FIG. 4. Rotation of the first link 104 causes the treatment tool elevator base 103 fixed to the rotation shaft 104a of the first link 104 to rotate integrally with the first link 104, thereby turning the treatment tool elevator base 103 into the elevated state.

Figure 7:
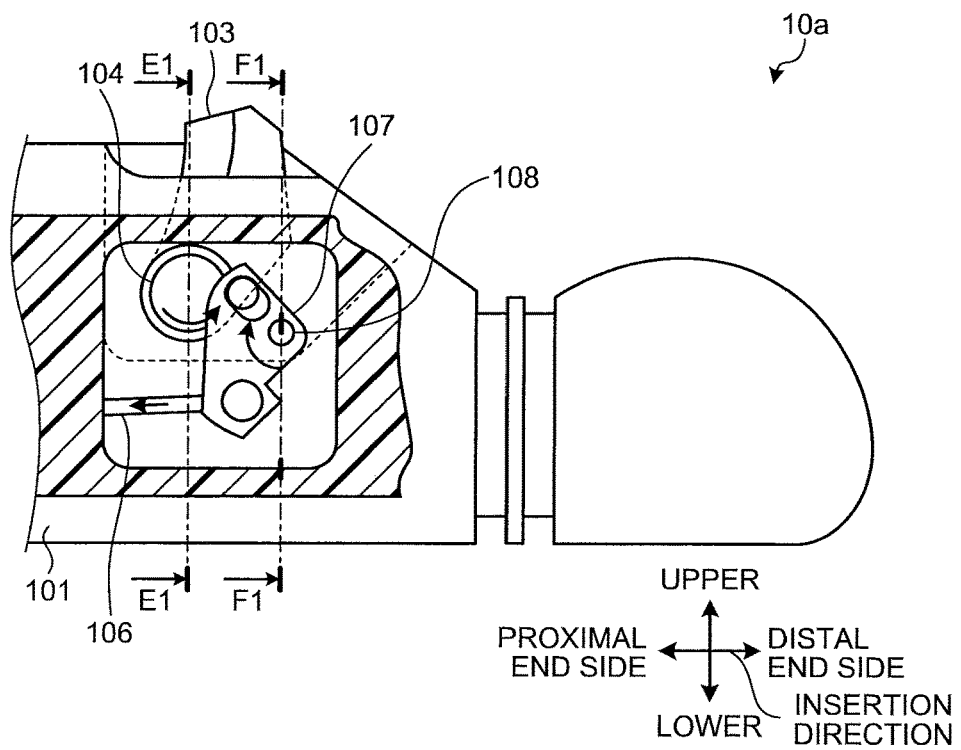
FIG. 7 is a diagram for illustrating an elevated state of a treatment tool elevator base.

FIG. 7 is a diagram for illustrating the elevated state of the treatment tool elevator base. When the wire 106 is pulled toward the proximal end side by the operation of the operating portion 11, each portion moves from the position in FIG. 4 in the direction of each of arrows in FIG. 7 in conjunction with the wire 106, thereby turning the treatment tool elevator base 103 into the elevated state illustrated in FIG. 7.

Moreover, in a case where the treatment tool elevator base 103 of the ultrasound endoscope 2 is rotated from the elevated state to the initial state, it would be only required to press the wire 106 toward the distal end side by operating the operating portion 11. When the wire 106 is pressed toward the distal end side, the second link 107 is pulled in the right direction in FIG. 4 in conjunction with the wire 106. This operation then causes the second link 107 to rotate counterclockwise in FIG. 4 around the rotation shaft 108 as the axis. When the second link 107 rotates, the long hole 107c of the second link 107 is engaged with the engagement portion 104b of the first link 104, thereby rotating the first link 104 clockwise in FIG. 4. Rotation of the first link 104 causes the treatment tool elevator base 103 to rotate integrally with the first link 104, thereby allowing the treatment tool elevator base 103 to return to the initial state.

Figure 8:
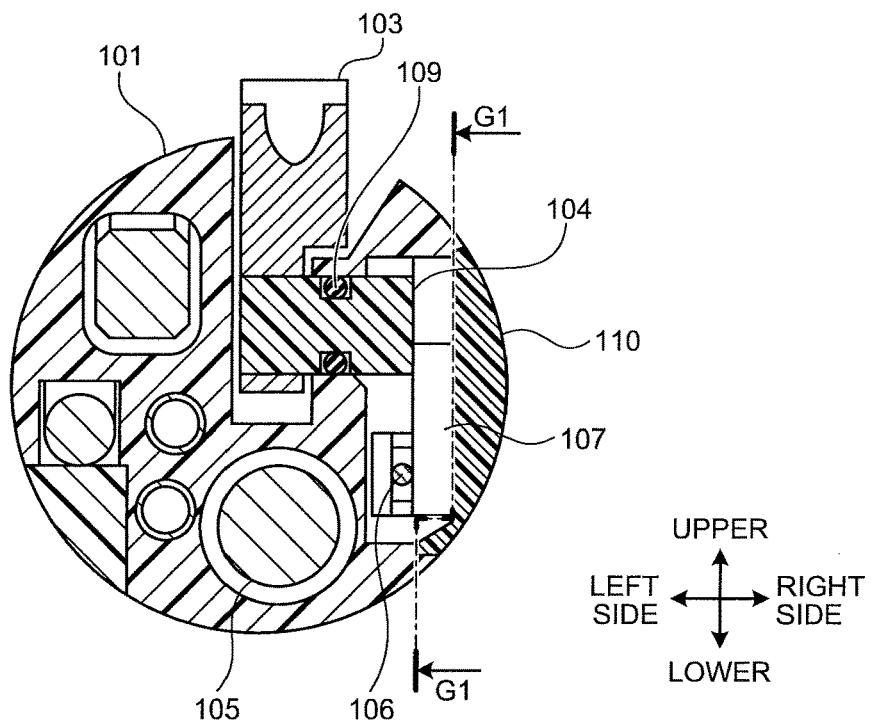
FIG. 8 is a cross-sectional view of the cross section taken along line E1-E1 in FIG. 7, viewed from the proximal end side.
Figure 9:
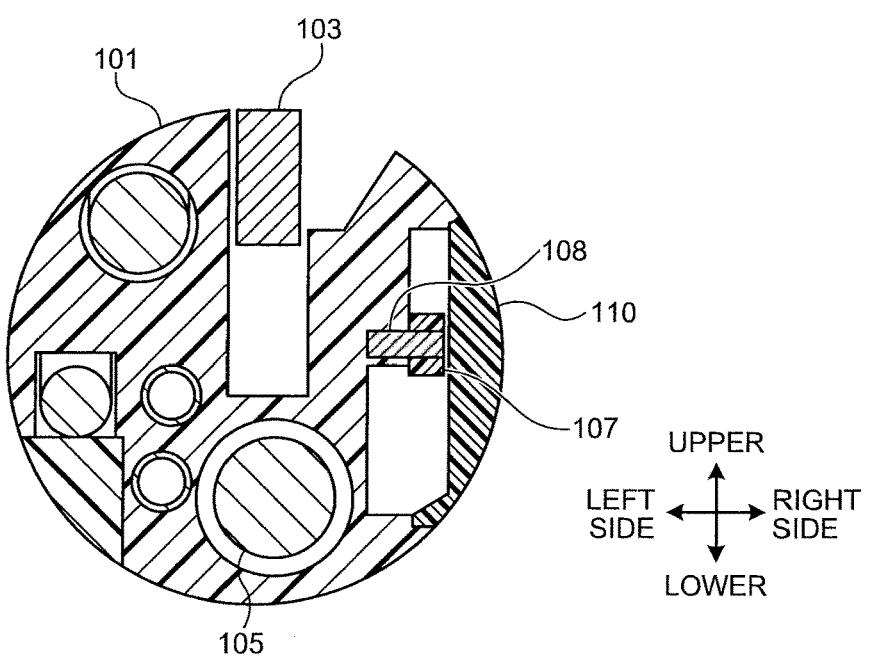
FIG. 9 is a cross-sectional view of the cross section taken along line F1-F1 in FIG. 7, viewed from the proximal end side.

FIG. 8 is a cross-sectional view of the cross section taken along line E1-E1 in FIG. 7, viewed from the proximal end side. FIG. 7 is a partial cross-sectional view of the cross section taken along line G1-G1 in FIG. 8, viewed from the right side. FIG. 9 is a cross-sectional view of the cross section taken along line F1-F1 in FIG. 7, viewed from the proximal end side. As illustrated in FIG. 8, watertightness of the portion between the first link 104 and the distal end rigid portion 101 is maintained by the O-ring 109 even when the treatment tool elevator base 103 rotates from the initial state to the elevated state.

Note that the ultrasound endoscope 2 has a gap G is provided between a lower portion of the treatment tool elevator base 103 and the distal end rigid portion 101, as illustrated in FIGS. 2 and 3. This arrangement enables cleaning by directly inserting a brush into this gap G during cleaning. That is, the ultrasound endoscope 2 is an ultrasound endoscope having a good cleaning efficiency. It is preferable that each of the widths W1 and W2 of the gap G is has a size that enables the brush to enter in view of cleaning efficiency. On the other hand, it is preferable that the each of the widths W1 and W2 of the gap G is not too great in view of miniaturization of the distal end portion 10a. From these demands, each of the widths W1 and W2 of the gap G is set to 0.5 mm or more and 2 mm or less.

Moreover, in the ultrasound endoscope 2, since the opening 101a of the distal end rigid portion 101 has a tapered shape, the brush easily accesses the lower portion of the treatment tool elevator base 103 and a portion around the rotation shaft 104a, leading to further enhancement in cleaning efficiency.

In the ultrasound endoscope 2, the wire connection portion 107b is located in a portion the lower than the reference plane P. Therefore, it is possible to provide the tapered shape in the opening 101a of the distal end rigid portion 101, and furthermore, with the presence of the gap G, it is also possible to suppress enlargement of the distal end of the insertion portion 10.

Furthermore, the ultrasound endoscope 2 is configured to maintain the operational feeling of the user accustomed to the operation of conventional endoscopes, so as to suppress discomfort during operation. In the ultrasound endoscope 2, when the wire 106 is pulled toward the proximal end side, the treatment tool 15 is elevated. Therefore, by inputting the similar operation as conventional endoscopes into the operating portion 11, the treatment tool 15 is elevated. This is because the operation transmission mechanism including the first link 104 and the second link 107 transmits operation such that the treatment tool 15 is elevated when the wire 106 is pulled toward the proximal end side. Moreover, the ultrasound endoscope 2 has a long distance between the shaft hole 107a and the wire connection portion 107b and a long distance between the shaft hole 107a and the long hole 107c, making it possible to reduce the force to be applied to the wire 106 in order to elevate the treatment tool 15. Therefore, in the ultrasound endoscope 2, since the user can elevate the treatment tool 15 by inputting similar operation as conventional endoscopes into the operating portion 11 with the same force, it is possible to maintain user's operational feeling.

As described above, the ultrasound endoscope 2 according to the first embodiment is an endoscope capable of enhancing cleaning efficiency without enlarging the distal end portion of the endoscope, and without deteriorating the user's operational feeling.

Second Embodiment

Figure 10:
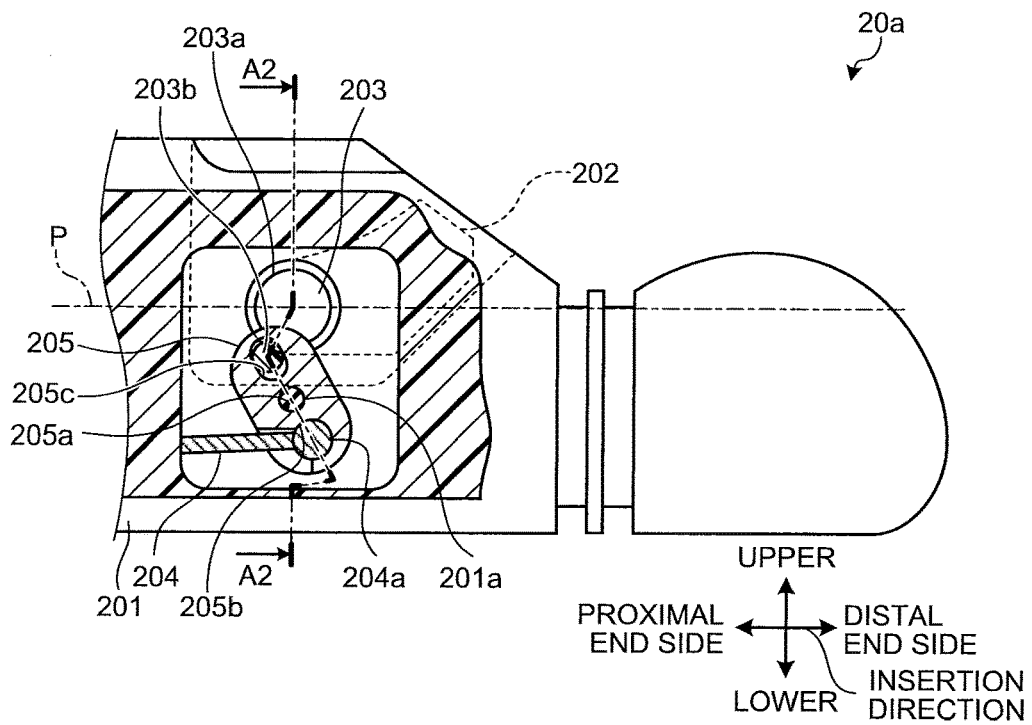
FIG. 10 is a schematic diagram illustrating a configuration of a main portion of an ultrasound diagnosis system including an ultrasound endoscope according to a second embodiment of the disclosure.
Figure 11:
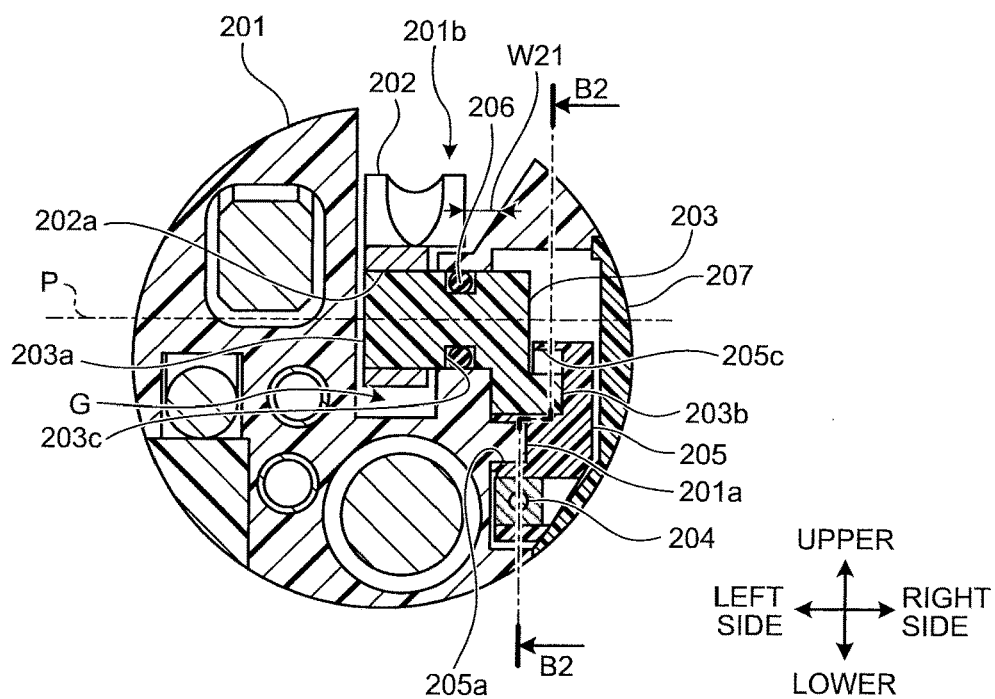
FIG. 11 is a cross-sectional view of the cross section taken along line A2-A2 in FIG. 10, viewed from the proximal end side.

Next, a second embodiment of the disclosure will be described. FIG. 10 is a schematic diagram illustrating a configuration of a main portion of an ultrasound diagnosis system including an ultrasound endoscope according to a second embodiment of the disclosure. FIG. 11 is a cross-sectional view of the cross section taken along line A2-A2 in FIG. 10, viewed from the proximal end side. FIG. 10 is a partial cross-sectional view of the cross section taken along line B2-B2 in FIG. 11, viewed from the right side.

The ultrasound endoscope according to the second embodiment is the same as the ultrasound endoscope 2 according to the first embodiment except for a distal end portion 20a. Furthermore, since the treatment tool channels, cables, or the like, of the ultrasound endoscope according to the second embodiment are also the same as the case of the ultrasound endoscope 2 according to the first embodiment, the description of these components will be appropriately omitted.

As illustrated in FIG. 10, the distal end portion 20a includes a distal end rigid portion 201, a treatment tool elevator base 202, a first link 203, a wire 204, and a second link 205. The treatment tool elevator base 202 elevates the treatment tool. The first link 203, as a first member, rotatably supports the treatment tool elevator base 202. The wire 204 transmits the operation input into the operating portion 11 to the distal end portion 20a. The second link 205, as a second member, transmits the operation from the wire 204 to the first link 203. Furthermore, as illustrated in FIG. 11, the distal end portion 20a includes an O-ring 206 and a cover 207. The O-ring 206 maintains a portion between the distal end rigid portion 201 and the first link 203 watertight. The cover 207 seals each of portions watertight.

As illustrated in FIG. 11, the distal end rigid portion 201 includes a rotation shaft 201a and an opening 201b for accommodating the treatment tool elevator base 202 in the initial state. A cross section of the opening 201b, which is a cross section orthogonal to the insertion direction, has a tapered shape with a width W21 in the left-right direction in FIG. 11 increasing in the upper direction in FIG. 11.

A shaft hole 202a is formed in the treatment tool elevator base 202 as illustrated in FIG. 11. The treatment tool elevator base 202 is rotatably supported by the first link 203 by fastening a rotation shaft 203a of the first link 203 to the shaft hole 202a with adhesion or a screw. Moreover, as illustrated in FIG. 11, a gap G similar to the gap G in the first embodiment is provided between the treatment tool elevator base 202 and the distal end rigid portion 201.

The first link 203 includes the rotation shaft 203a and an engagement portion 203b as a first engagement portion that is engaged with the second link 205 as illustrated in FIG. 10. Moreover, the first link 203 includes a groove 203c into which the O-ring 206 is fitted, as illustrated in FIG. 11.

The wire 204 is connected to the operating portion 11 on the proximal end side and is movable in the insertion direction by operation of the operating portion 11. A distal end portion 204a of the wire 204 is connected to a wire connection portion 205b of the second link 205, as illustrated in FIG. 10. Moreover, the wire 204 is connected to a portion in the lower direction in FIG. 11 with respect to the reference plane P (refer to FIGS. 10 and 11).

The second link 205 includes a shaft hole 205a through which the rotation shaft 201a is inserted, and is rotatably supported with respect to the rotation shaft 201a. Moreover, the second link 205 includes the wire connection portion 205b as illustrated in FIG. 10. The wire connection portion 205b slidably supports the distal end portion 204a of the wire 204. Furthermore, a long hole 205c as a second engagement portion is formed in the second link 205, as illustrated in FIG. 10. The long hole 205c is engaged with the engagement portion 203b of the first link 203, thereby transmitting the operation from the wire 204 to the first link 203.

Note that the first link 203 and the second link 205 function as an operation transmission mechanism for transmitting the operation input from the wire 204. The operation transmission mechanism converts the direction of transmitting the operation input from the wire 204 and transmits the operation such that the rotation shaft 203a rotates in a direction of elevating the treatment tool.

As illustrated in FIG. 11, the O-ring 206 is fitted into the groove 203c of the first link 203 to maintain a portion between the distal end rigid portion 201 and the first link 203 watertight. The cover 207 has a shape slightly larger than the opening of the distal end rigid portion 201 and is fixed to the distal end rigid portion 201 by adhesion, or the like. Additionally, the O-ring 206 and the cover 207 maintain watertightness in a region including the engagement portion 203b, the wire 204, and the second link 205 from the right side of the groove 203c of the first link 203 in FIG. 11. As a result of this arrangement, these watertight regions are regions to which no dirt adheres at the use of the ultrasound endoscope, and thus, regions for which no cleaning is needed.

Next, the operation of rotating the treatment tool elevator base 202 of the ultrasound endoscope according to the second embodiment from the initial state to the elevated state will be described. First, when the wire 204 is pulled to the proximal end side by the operation of the operating portion 11 in the initial state of FIG. 10, the second link 205 rotates clockwise in FIG. 10 around the rotation shaft 201a as an axis in conjunction with the wire 204. When the second link 205 rotates, the long hole 205c of the second link 205 is engaged with the engagement portion 203b of the first link 203, thereby rotating the first link 203 counterclockwise in FIG. 10. Rotation of the first link 203 causes the treatment tool elevator base 202 fixed to the rotation shaft 203a of the first link 203 to rotate integrally with the first link 203, thereby turning the treatment tool elevator base 202 into the elevated state.

Figure 12:
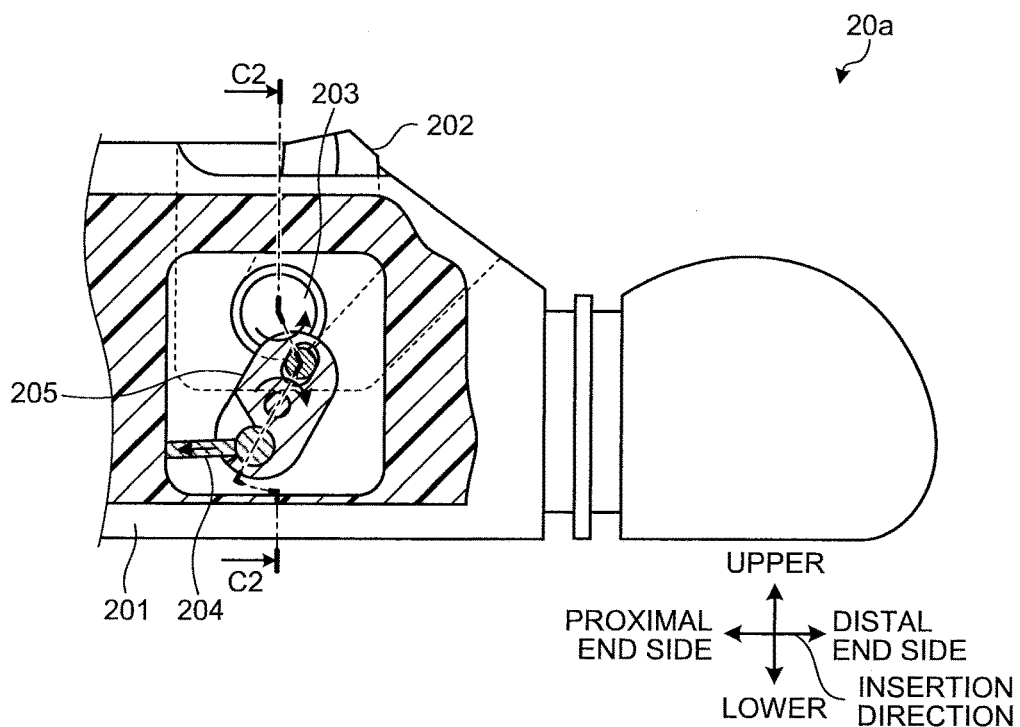
FIG. 12 is a diagram for illustrating an elevated state of the treatment tool elevator base.

FIG. 12 is a view for illustrating the elevated state of the treatment tool elevator base. When the wire 204 is pulled toward the proximal end side by the operation of the operating portion 11, each portion moves from the position of FIG. 10 in the direction of each of arrows in FIG. 12 in conjunction with the wire 204, thereby turning the treatment tool elevator base 202 into the elevated state illustrated in FIG. 12.

Figure 13:
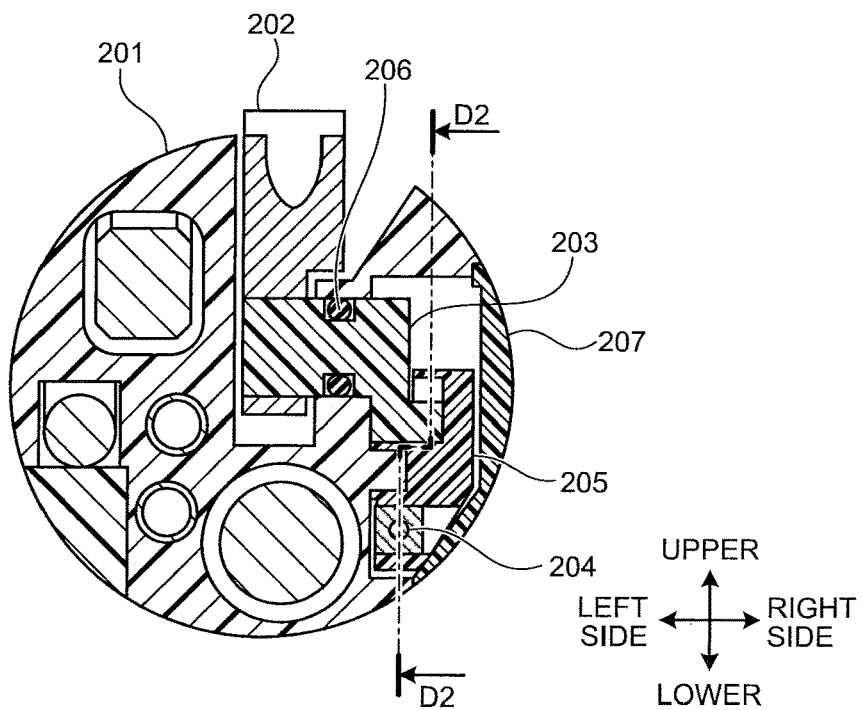
FIG. 13 is a cross-sectional view of the cross section taken along line C2-C2 in FIG. 12, viewed from the proximal end side.

FIG. 13 is a cross-sectional view of the cross section taken along line C2-C2 in FIG. 12, viewed from the proximal end side. FIG. 12 is a partial cross-sectional view of the cross section taken along line D2-D2 in FIG. 13, viewed from the right side. As illustrated in FIG. 13, watertightness of the portion between the first link 203 and the distal end rigid portion 201 is maintained by the O-ring 206 even when the treatment tool elevator base 202 rotates from the initial state to the elevated state.

Note that, as illustrated in FIG. 11, the ultrasound endoscope according to the second embodiment has the gap G provided between a lower portion of the treatment tool elevator base 202 and the distal end rigid portion 201. The size of the gap G is the same as the case of the first embodiment. This arrangement enables cleaning by directly inserting a brush into this gap G during cleaning. That is, this ultrasound endoscope is an ultrasound endoscope having a good cleaning efficiency.

Moreover, in the ultrasound endoscope, since the opening 201b of the distal end rigid portion 201 has a tapered shape, the brush easily accesses the lower portion of the treatment tool elevator base 202 and a portion around the rotation shaft 203a, leading to further enhancement in cleaning efficiency.

Moreover, in the ultrasound endoscope, the wire connection portion 205b is located at a portion lower than the reference plane P. Therefore, it is possible to provide the tapered shape in the opening 201b of the distal end rigid portion 201, and furthermore, with the presence of the gap G, it is also possible to suppress enlargement of the distal end of the insertion portion 10.

Furthermore, the ultrasound endoscope is configured to maintain the operational feeling of the user accustomed to the operation of conventional endoscopes, so as to suppress discomfort during operation. In this ultrasound endoscope, when the wire 204 is pulled toward the proximal end side, the treatment tool is elevated. Therefore, it is possible to elevate the treatment tool by the same operation as the conventional endoscope. This is because the operation transmission mechanism including the first link 203 and the second link 205 transmits operation such that the treatment tool is elevated when the wire 204 is pulled toward the proximal end side. As illustrated with the ultrasound endoscope, the operation transmission mechanism may include a link. Moreover, the ultrasound endoscope has a long distance between the shaft hole 205a and the wire connection portion 205b and a long distance between the shaft hole 205a and the long hole 205c, making it possible to reduce the force to be applied to the wire 204 in order to elevate the treatment tool. Therefore, user's operational feeling of the user is maintained with the ultrasound endoscope.

As described above, the ultrasound endoscope according to the second embodiment is an endoscope capable of enhancing cleaning efficiency without enlarging the distal end portion of the endoscope, and without deteriorating the user's operational feeling.

Third Embodiment

Figure 14:
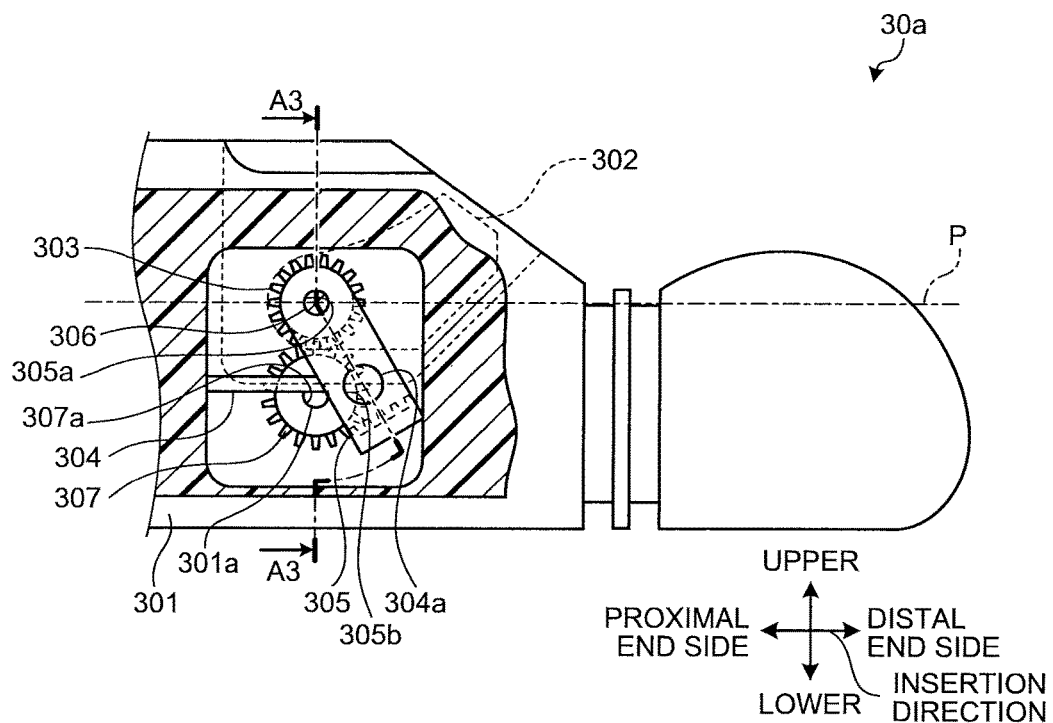
FIG. 14 is a schematic diagram illustrating a configuration of a main portion of an ultrasound diagnosis system including an ultrasound endoscope according to a third embodiment of the disclosure.
Figure 15:
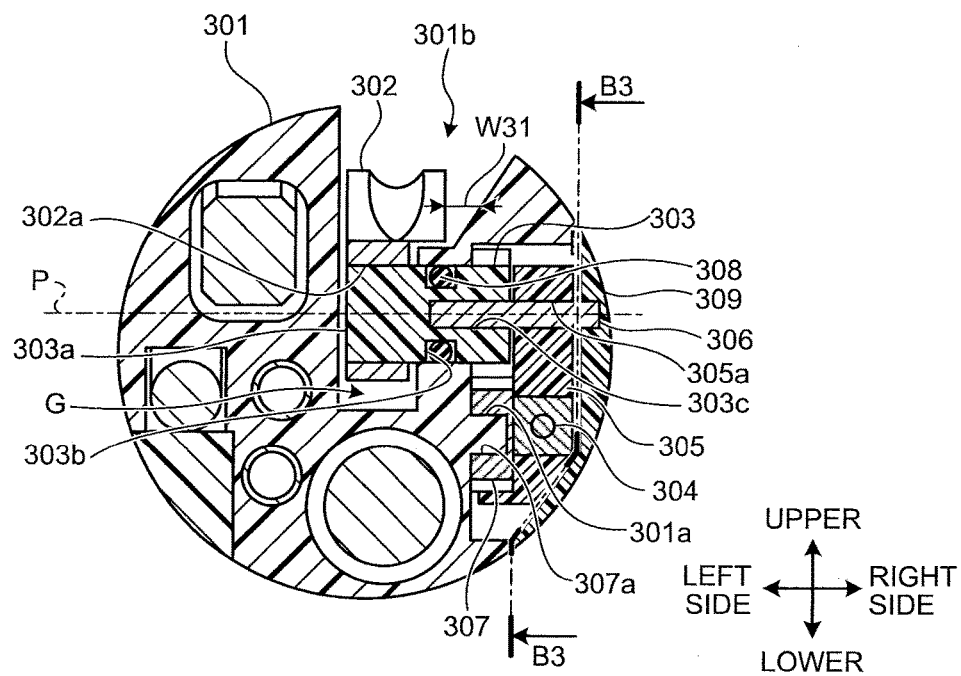
FIG. 15 is a cross-sectional view of the cross section taken along line A3-A3 in FIG. 14, viewed from the proximal end side.

Next, a third embodiment of the disclosure will be described. FIG. 14 is a schematic diagram illustrating a configuration of a main portion of an ultrasound diagnosis system including an ultrasound endoscope according to the third embodiment of the disclosure. FIG. 15 is a cross-sectional view of the cross section taken along line A3-A3 of FIG. 14, viewed from the proximal end side. FIG. 14 is a partial cross-sectional view of the cross section taken along line B3-B3 in FIG. 15, viewed from the right side.

The ultrasound endoscope according to the third embodiment is the same as the ultrasound endoscope 2 according to the first embodiment except for a distal end portion 30a. Furthermore, since the treatment tool channel, the cable, and the like, of the ultrasound endoscope according to the third embodiment are also the same as the ultrasound endoscope 2 according to the first embodiment, description of these components will be appropriately omitted.

As illustrated in FIG. 14, the distal end portion 30a includes a distal end rigid portion 301, a treatment tool elevator base 302, a first gear 303, a wire 304, an internal geared arm 305, a rotation shaft 306, and a second gear 307. The treatment tool elevator base 302 elevates the treatment tool. The first gear 303 rotatably supports the treatment tool elevator base 302. The wire 304 transmits the operation input into the operating portion 11 to the insertion portion 10. Operation from the wire 304 is input into the internal geared arm 305. The rotation shaft 306 rotatably supports the internal geared arm 305. The second gear 307 transmits the operation from the internal geared arm 305 to the first gear 303. Furthermore, as illustrated in FIG. 15, the distal end portion 30a includes an O-ring 308 and a cover 309. The O-ring 308 maintains a portion between the distal end rigid portion 301 and the first gear 303 watertight. The cover 309 seals each of portions watertight.

As illustrated in FIG. 15, the distal end rigid portion 301 includes a rotation shaft 301a and an opening 301b for accommodating the treatment tool elevator base 302 in the initial state. A cross section of the opening 301b, which is a cross section orthogonal to the insertion direction, has a tapered shape with a width W31 in the left-right direction in FIG. 15 increasing in the upper direction in FIG. 15.

A shaft hole 302a is formed in the treatment tool elevator base 302 as illustrated in FIG. 15. The treatment tool elevator base 302 is rotatably supported by the first gear 303 by fastening a rotation shaft 303a of the first gear 303 to the shaft hole 302a with adhesion or a screw. Moreover, a gap G similar to the gap G in the first embodiment is provided between the treatment tool elevator base 302 and the distal end rigid portion 301.

The first gear 303 includes the rotation shaft 303a. Moreover, the first gear 303 includes a groove 303b into which the O-ring 308 is fitted, as illustrated in FIG. 15. Furthermore, the first gear 303 includes a shaft hole 303c into which the rotation shaft 306 is inserted.

The wire 304 is connected to the operating portion 11 on the proximal end side and is movable in the insertion direction by operation of the operating portion 11. A distal end portion 304a of the wire 304 is connected to a wire connection portion 305b of the second gear 307 as illustrated in FIG. 14. Moreover, the wire 304 is connected to a portion in the lower direction of FIG. 15 with respect to the reference plane P (refer to FIGS. 14 and 15).

The internal geared arm 305 includes a shaft hole 305a through which the rotation shaft 306 is inserted, and is rotatably supported with respect to the rotation shaft 306. Moreover, the internal geared arm 305 includes the wire connection portion 305b.

As illustrated in FIG. 15, one end of the rotation shaft 306 is fixed to the shaft hole 303c of the first gear 303 with adhesion, or the like, and rotatably supports the internal geared arm 305. Note that it is only required to configure such that the rotation shaft 306 is fixed to any of the first gear 303, the internal geared arm 305, and the cover 309 by adhesion, or the like, and that the first gear 303 and the internal geared arm 305 are rotatable independently of each other.

The second gear 307 includes a shaft hole 307a through which the rotation shaft 301a is inserted, and is rotatably supported with respect to the rotation shaft 301a. Moreover, the second gear 307 meshes with the first gear 303 and the internal geared arm 305, thereby transmitting the operation transmitted from the internal geared arm 305 to the first gear 303.

Note that the first gear 303, the internal geared arm 305, and the second gear 307 function as an operation transmission mechanism for transmitting the operation input from the wire 304. The operation transmission mechanism converts the direction of transmitting the operation input from the wire 304 and transmits the operation such that the rotation shaft 303a rotates in a direction of elevating the treatment tool.

As illustrated in FIG. 15, the O-ring 308 is fitted into the groove 303b of the first gear 303 to maintain the portion between the distal end rigid portion 301 and the first gear 303 watertight. The cover 309 has a shape slightly larger than the opening of the distal end rigid portion 301 and is fixed to the distal end rigid portion 301 by adhesion, or the like. Additionally, the O-ring 308 and the cover 309 maintain watertightness in a region including the wire 304, the internal geared arm 305, and the second gear 307 from the right side of the groove 303b of the first gear 303 in FIG. 15. As a result of this arrangement, these watertight regions are regions to which no dirt adheres at the use of the ultrasound endoscope, and thus, regions for which no cleaning is needed.

Next, the operation of rotating the treatment tool elevator base 302 of the ultrasound endoscope according to the third embodiment from the initial state to the elevated state will be described. First, when the wire 304 is pulled to the proximal end side by the operation of the operating portion 11 in the initial state of FIG. 14, the internal geared arm 305 rotates clockwise in FIG. 14 around the rotation shaft 306 as an axis in conjunction with the wire 304. With engagement between the internal geared arm 305 and the second gear 307, the second gear 307 rotates clockwise in FIG. 14 around the rotation shaft 301*a* as an axis in conjunction with the internal geared arm 305. Furthermore, with engagement between the second gear 307 and the first gear 303, the first gear 303 rotates counterclockwise in FIG. 14 around the rotation shaft 303*a* as an axis in conjunction with the second gear 307. Rotation of the first gear 303 causes the treatment tool elevator base 302 fixed to the rotation shaft 303*a* of the first gear 303 to rotate integrally with the first gear 303, thereby turning the treatment tool elevator base 302 into the elevated state.

Figure 16:
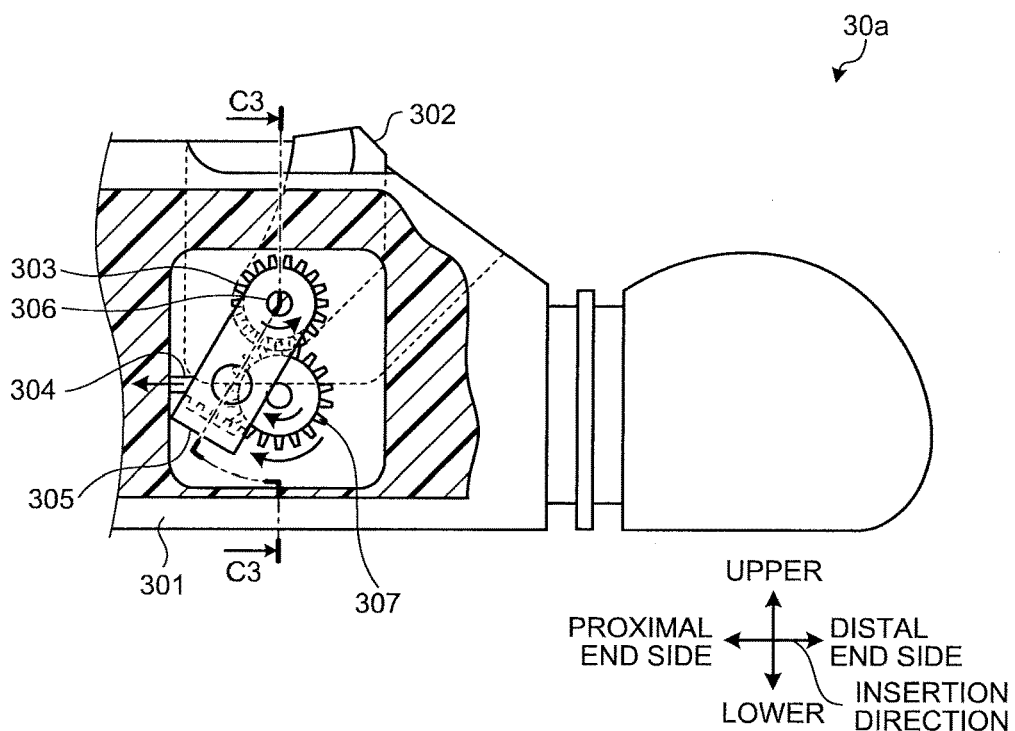
FIG. 16 is a diagram for illustrating an elevated state of the treatment tool elevator base.

FIG. 16 is a view for illustrating the elevated state of the treatment tool elevator base. When the wire 304 is pulled toward the proximal end side by the operation of the operating portion 11, each portion moves from the position of FIG. 14 in the direction of each of arrows in FIG. 16 in conjunction with the wire 304, thereby turning the treatment tool elevator base 302 into the elevated state illustrated in FIG. 16.

Figure 17:
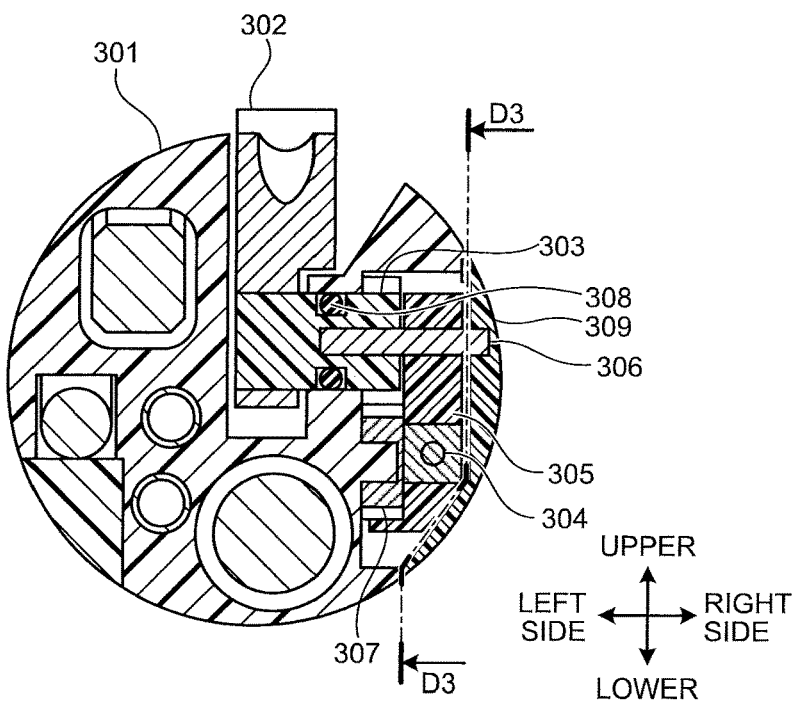
FIG. 17 is a cross-sectional view of the cross section taken along line C3-C3 in FIG. 16, viewed from the proximal end side.

FIG. 17 is a cross-sectional view of the cross section taken along line C3-C3 in FIG. 16, viewed from the proximal end side. FIG. 16 is a partial cross-sectional view of the cross section taken along line D3-D3 in FIG. 17, viewed from the right side. As illustrated in FIG. 17, watertightness of the portion between the first gear 303 and the distal end rigid portion 301 is maintained by the O-ring 308 even when the treatment tool elevator base 302 rotates from the initial state to the elevated state.

Note that, as illustrated in FIG. 15, the ultrasound endoscope according to the third embodiment has the gap G provided between a lower portion of the treatment tool elevator base 302 and the distal end rigid portion 301. The size of the gap G is the same as the case of the first embodiment. This arrangement enables cleaning by directly inserting a brush into this gap G during cleaning. That is, this ultrasound endoscope is an ultrasound endoscope having a good cleaning efficiency.

Moreover, in the ultrasound endoscope, since the opening 301*b* of the distal end rigid portion 301 has a tapered shape, the brush easily accesses the lower portion of the treatment tool elevator base 302 and a portion around the rotation shaft 303*a*, leading to further enhancement in cleaning efficiency.

Moreover, in this ultrasound endoscope, the wire connection portion 305*b* is located at a portion lower than the reference plane P. Therefore, it is possible to provide the tapered shape in the opening 301*b* of the distal end rigid portion 301, and furthermore, with the presence of the gap G, it is also possible to suppress enlargement of the distal end of the insertion portion 10.

Furthermore, the ultrasound endoscope is configured to maintain the operational feeling of the user accustomed to the operation of conventional endoscopes, so as to suppress discomfort during operation. In this ultrasound endoscope, when the wire 304 is pulled toward the proximal end side, the treatment tool is elevated. Therefore, it is possible to elevate the treatment tool by the same operation as the conventional endoscope. This is because the operation transmission mechanism including the first gear 303, the internal geared arm 305, and the second gear 307 transmits the operation such that the treatment tool is elevated when the wire 304 is pulled toward the proximal end side. As illustrated with the ultrasound endoscope, the operation transmission mechanism may include an arm and a gear. Moreover, the ultrasound endoscope has a long distance between the shaft hole 305*a* and the wire connection portion 305*b* and a long distance between the axis of the first gear 303 and the axis of the second gear 307, making it possible to reduce the force to be applied to the wire 304 in order to elevate the treatment tool. Therefore, user's operational feeling of the user is maintained with the ultrasound endoscope.

As described above, the ultrasound endoscope according to the third embodiment is an endoscope capable of enhancing cleaning efficiency without enlarging the distal end portion of the endoscope, and without deteriorating the user's operational feeling.

Fourth Embodiment

Figure 18:
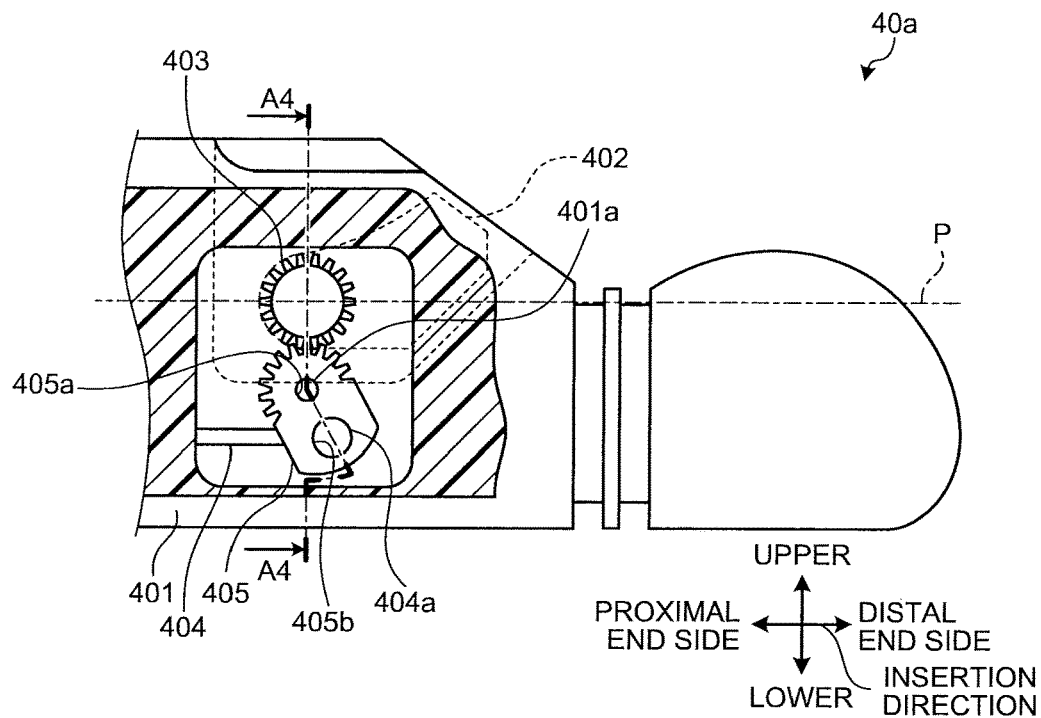
FIG. 18 is a schematic diagram illustrating a configuration of a main portion of an ultrasound diagnosis system including an ultrasound endoscope according to a fourth embodiment of the disclosure.
Figure 19:
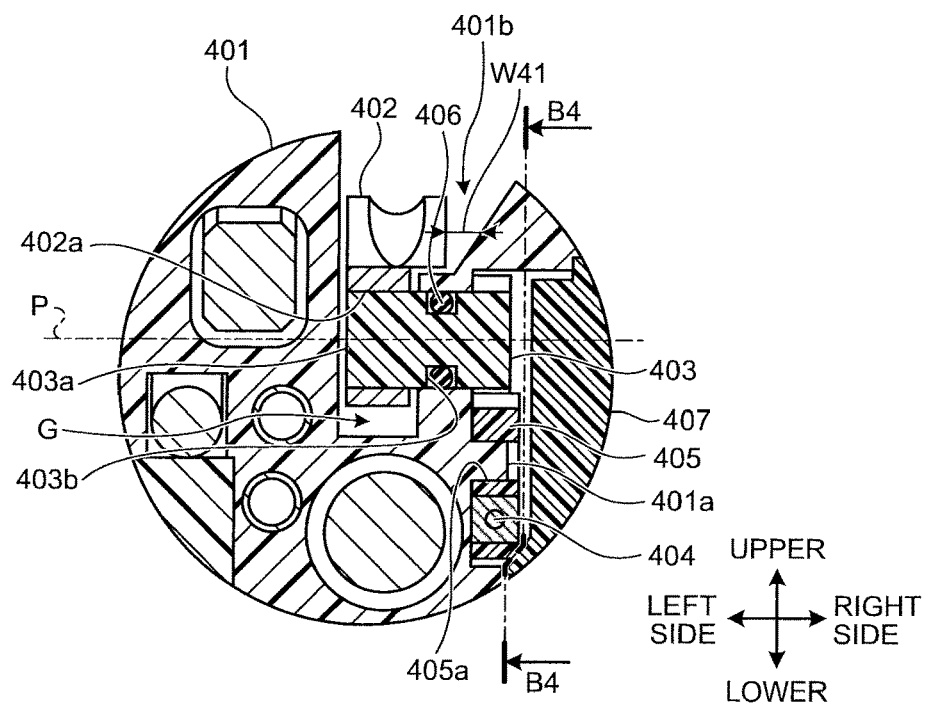
FIG. 19 is a cross-sectional view of the cross section taken along line A4-A4 in FIG. 18, viewed from the proximal end side.

Next, a fourth embodiment of the disclosure will be described. FIG. 18 is a schematic diagram illustrating a configuration of a main portion of an ultrasound diagnosis system including an ultrasound endoscope according to the fourth embodiment of the disclosure. FIG. 19 is a cross-sectional view of the cross section taken along line A4-A4 in FIG. 18, viewed from the proximal end side. FIG. 18 is a partial cross-sectional view of the cross section taken along line B4-B4 in FIG. 19, viewed from the right side.

The ultrasound endoscope according to the fourth embodiment is the same as the ultrasound endoscope 2 according to the first embodiment except for a distal end portion 40*a*. Furthermore, since the treatment tool channel, the cable, or the like, of the ultrasound endoscope according to the fourth embodiment are also the same as the ultrasound endoscope 2 according to the first embodiment, the description of these components will be appropriately omitted.

As illustrated in FIG. 18, the distal end portion 40*a* includes a distal end rigid portion 401, a treatment tool elevator base 402, a gear 403, a wire 404, and a geared arm 405. The treatment tool elevator base 402 elevates the treatment tool. The gear 403 rotatably supports the treatment tool elevator base 402. The wire 404 transmits the operation input into the operating portion 11 to the insertion portion 10. The geared arm 405 transmits the operation from the wire 404 to the gear 403. Furthermore, as illustrated in FIG. 19, the distal end portion 40*a* includes an O-ring 406 and a cover 407. The O-ring 406 maintains a portion between the distal end rigid portion 401 and the gear 403 watertight. The cover 407 seals each of portions watertight.

As illustrated in FIG. 19, the distal end rigid portion 401 includes a rotation shaft 401*a* and an opening 401*b* for accommodating the treatment tool elevator base 402 in the initial state. A cross section of the opening 401*b*, which is a cross section orthogonal to the insertion direction, has a tapered shape with a width W41 in the left-right direction in FIG. 19 increasing in the upper direction in FIG. 19.

A shaft hole 402*a* is formed in the treatment tool elevator base 402 as illustrated in FIG. 19. The treatment tool elevator base 402 is rotatably supported by the gear 403 by fastening a rotation shaft 403*a* of the gear 403 to the shaft hole 402*a* with adhesion or a screw. Moreover, a gap G similar to the gap G in the first embodiment is provided between the treatment tool elevator base 402 and the distal end rigid portion 401.

The gear 403 includes the rotation shaft 403a. Moreover, the gear 403 includes a groove 403b into which the O-ring 406 is fitted, as illustrated in FIG. 19.

The wire 404 is connected to the operating portion 11 on the proximal end side and is movable in the insertion direction by operation of the operating portion 11. A distal end portion 404a of the wire 404 is connected to a wire connection portion 405b of the geared arm 405 as illustrated in FIG. 18. Moreover, the wire 404 is connected to a lower portion in FIG. 19 with respect to the reference plane P (refer to FIGS. 18 and 19).

The geared arm 405 includes a shaft hole 405a through which the rotation shaft 401a is inserted, and is rotatably supported with respect to the rotation shaft 401a. Moreover, the geared arm 405 includes the wire connection portion 405b. The geared arm 405 meshes with the gear 403, thereby transmitting the operation input from the wire 404 to the gear 403.

Note that the gear 403 and the geared arm 405 function as an operation transmission mechanism for transmitting the operation input from the wire 404. The operation transmission mechanism converts the direction of transmitting the operation input from the wire 404 and transmits the operation such that the rotation shaft 403a rotates in a direction of elevating the treatment tool.

As illustrated in FIG. 19, the O-ring 406 is fitted into the groove 403b of the gear 403 to maintain the portion between the distal end rigid portion 401 and the gear 403 watertight. The cover 407 has a shape slightly larger than the opening of the distal end rigid portion 401 and is fixed to the distal end rigid portion 401 by adhesion, or the like. Additionally, the O-ring 406 and the cover 407 maintain watertightness in a region including the wire 404 and the internal geared arm 405 from the right side of the groove 403b of the gear 403 in FIG. 19. As a result of this arrangement, these watertight regions are regions to which no dirt adheres at the use of the ultrasound endoscope, and thus, regions for which no cleaning is needed.

Next, the operation of rotating the treatment tool elevator base 402 of the ultrasound endoscope according to the fourth embodiment from the initial state to the elevated state will be described. First, when the wire 404 is pulled to the proximal end side by the operation of the operating portion 11 in the initial state of FIG. 18, the geared arm 405 rotates clockwise in FIG. 18 around the rotation shaft 401a as an axis in conjunction with the wire 404. Then, with engagement between the geared arm 405 and the gear 403, the gear 403 rotates counterclockwise in FIG. 18 around the rotation shaft 403a as an axis in conjunction with the geared arm 405. Rotation of the gear 403 causes the treatment tool elevator base 402 fixed to the rotation shaft 403a of the gear 403 to rotate integrally with the gear 403, thereby turning the treatment tool elevator base 402 into the elevated state.

Figure 20:
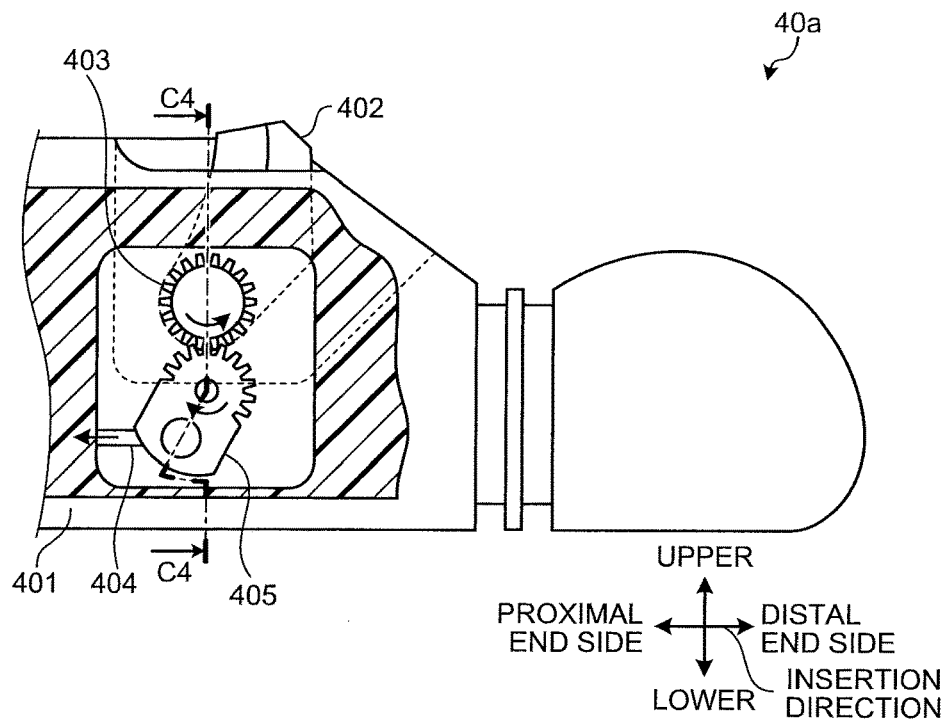
FIG. 20 is a diagram for illustrating an elevated state of the treatment tool elevator base.

FIG. 20 is a view for illustrating an elevated state of the treatment tool elevator base. When the wire 404 is pulled toward the proximal end side by the operation of the operating portion 11, each portion moves from the position of FIG. 18 in the direction of each of arrows in FIG. 20 in conjunction with the wire 404, thereby turning the treatment tool elevator base 402 into the elevated state illustrated in FIG. 20.

Figure 21:
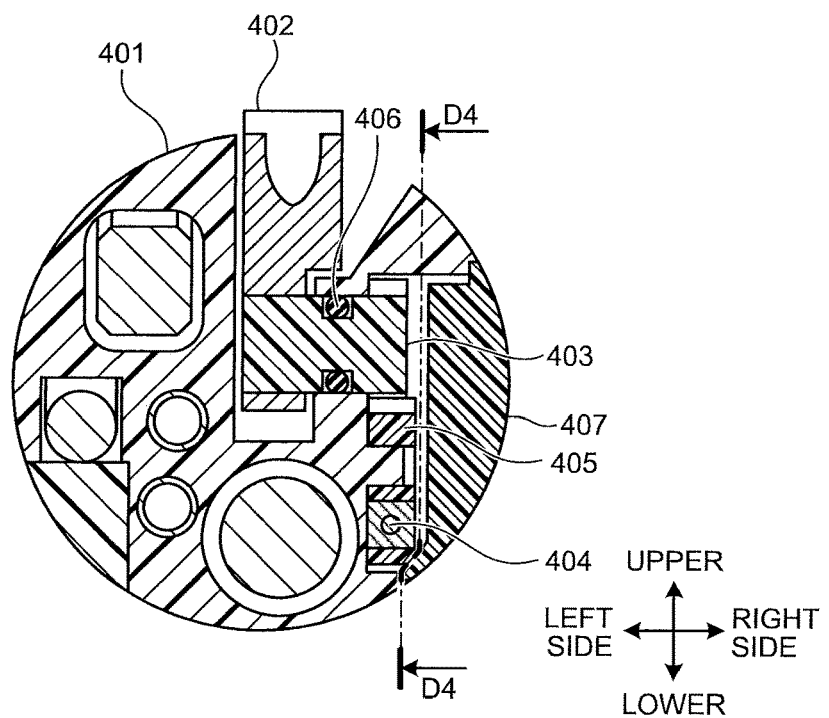
FIG. 21 is a cross-sectional view of the cross section taken along line C4-C4 in FIG. 20, viewed from the proximal end side.

FIG. 21 is a cross-sectional view of the cross section taken along line C4-C4 in FIG. 20, viewed from the proximal end side. FIG. 20 is a partial cross-sectional view of the cross section taken along line D4-D4 in FIG. 21, viewed from the right side. As illustrated in FIG. 21, watertightness of the portion between the gear 403 and the distal end rigid portion 401 is maintained by the O-ring 406 even when the treatment tool elevator base 402 rotates from the initial state to the elevated state.

Note that, as illustrated in FIG. 19, the ultrasound endoscope according to the fourth embodiment has the gap G provided between a lower portion of the treatment tool elevator base 402 and the distal end rigid portion 401. The size of the gap G is the same as the case of the first embodiment. This arrangement enables cleaning by directly inserting a brush into this gap G during cleaning. That is, this ultrasound endoscope is an ultrasound endoscope having a good cleaning efficiency.

Moreover, in the ultrasound endoscope, since the opening 401b of the distal end rigid portion 401 has a tapered shape, the brush easily accesses the lower portion of the treatment tool elevator base 402 and a portion around the rotation shaft 403a, leading to further enhancement in cleaning efficiency.

Moreover, in this ultrasound endoscope, the wire connection portion 405b is located at a portion lower than the reference plane P. Therefore, it is possible to provide the tapered shape in the opening 401b of the distal end rigid portion 401, and furthermore, with the presence of the gap G, it is also possible to suppress enlargement of the distal end of the insertion portion 10.

Furthermore, the ultrasound endoscope is configured to maintain the operational feeling of the user accustomed to the operation of conventional endoscopes, so as to suppress discomfort during operation. In this ultrasound endoscope, when the wire 404 is pulled toward the proximal end side, the treatment tool is elevated. Therefore, it is possible to elevate the treatment tool by the same operation as the conventional endoscope. This is because the operation transmission mechanism including the gear 403 and the geared arm 405 transmits the operation such that the treatment tool elevated when the wire 404 is pulled toward the proximal end side. As illustrated with the ultrasound endoscope, the operation transmission mechanism may include an arm and a gear. Moreover, the ultrasound endoscope has a long distance between the shaft hole 402a and the wire connection portion 405b and a long distance between the axis of the gear 403 and the axis of the geared arm 405, making it possible to reduce the force to be applied to the wire 404 in order to elevate the treatment tool. Therefore, user's operational feeling of the user is maintained with the ultrasound endoscope.

As described above, the ultrasound endoscope according to the fourth embodiment is an endoscope capable of enhancing cleaning efficiency without enlarging the distal end portion of the endoscope, and without deteriorating the user's operational feeling.

Fifth Embodiment

Figure 22:
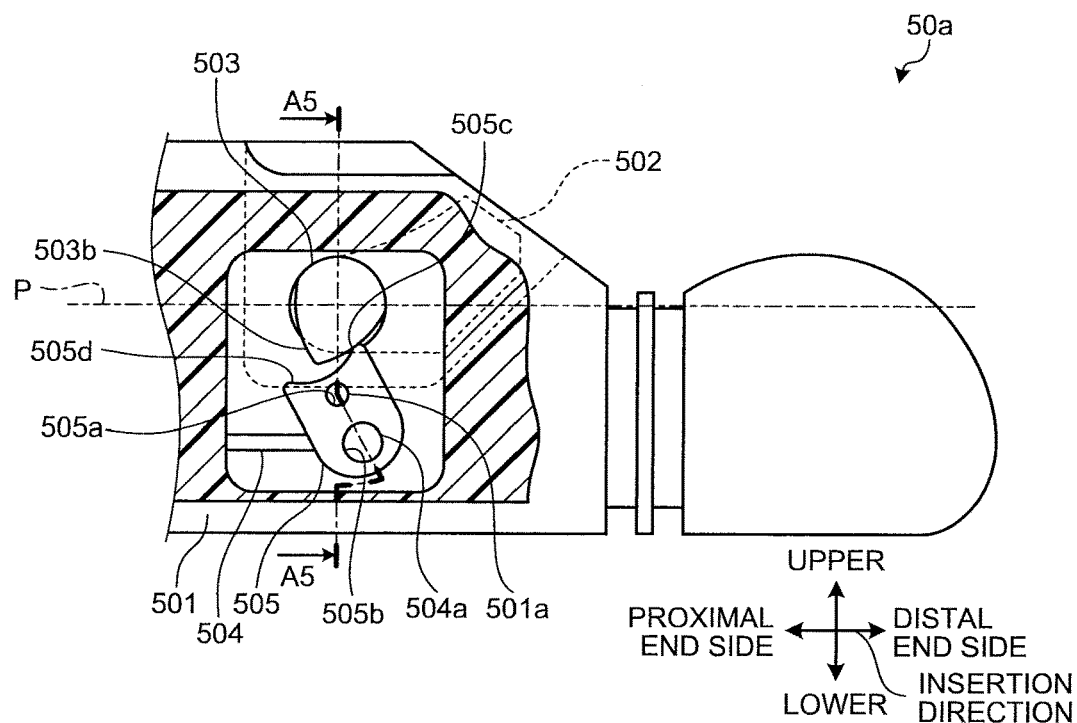
FIG. 22 is a schematic diagram illustrating a configuration of a main portion of an ultrasound diagnosis system including an ultrasound endoscope according to a fifth embodiment of the disclosure.
Figure 23:
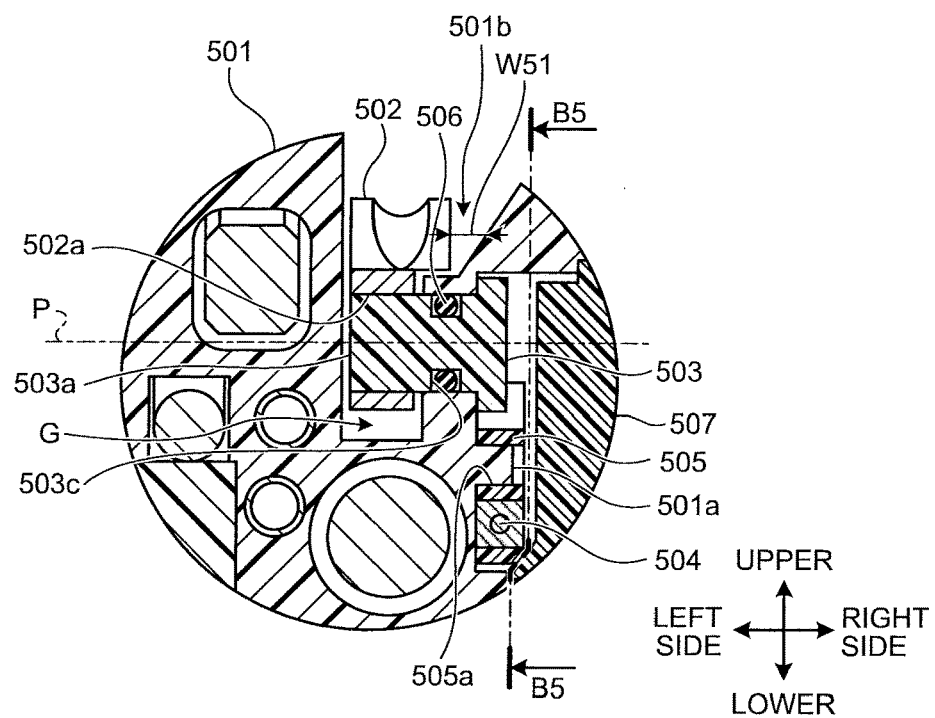
FIG. 23 is a cross-sectional view of the cross section taken along line A5-A5 in FIG. 22, viewed from the proximal end side.

Next, a fifth embodiment of the disclosure will be described. FIG. 22 is a schematic diagram illustrating a configuration of a main portion of an ultrasound diagnosis system including an ultrasound endoscope according to the fifth embodiment of the disclosure. FIG. 23 is a cross-sectional view taken along line A5-A5 in FIG. 22, viewed from the proximal end side. FIG. 22 is a partial cross-sectional view of the cross section taken along line B5-B5 in FIG. 23, viewed from the right side.

The ultrasound endoscope according to the fifth embodiment is the same as the ultrasound endoscope 2 according to the first embodiment except for a distal end portion 50a. Furthermore, since the treatment tool channel, the cable, or the like, of the ultrasound endoscope according to the fifth embodiment are also the same as the ultrasound endoscope 2 according to the first embodiment, the description of these components will be appropriately omitted.

As illustrated in FIG. 22, the distal end portion 50a includes a distal end rigid portion 501, a treatment tool elevator base 502, a first cam 503, a wire 504, and a second cam 505. The treatment tool elevator base 502 elevates the treatment tool. The first cam 503 rotatably supports the treatment tool elevator base 502. The wire 504 transmits the operation input into the operating portion 11 to the insertion portion 10. The second cam 505 transmits the operation from the wire 504 to the first cam 503. Furthermore, as illustrated in FIG. 23, the distal end portion 50a includes an O-ring 506 and a cover 507. The O-ring 506 maintains a portion between the distal end rigid portion 501 and the first cam 503 watertight. The cover 507 seals each of portions watertight.

As illustrated in FIG. 23, the distal end rigid portion 501 includes a rotation shaft 501a and an opening 501b for accommodating the treatment tool elevator base 502 in the initial state. A cross section of the opening 501b, which is a cross section orthogonal to the insertion direction, has a tapered shape with a width W51 in the left-right direction in FIG. 23 increasing in the upper direction in FIG. 23.

A shaft hole 502a is formed in the treatment tool elevator base 502 as illustrated in FIG. 23. The treatment tool elevator base 502 is rotatably supported by the first cam 503 by fastening a rotation shaft 503a of the first cam 503 to the shaft hole 502a with adhesion or a screw. Moreover, a gap G similar to the gap G in the first embodiment is provided between the treatment tool elevator base 502 and the distal end rigid portion 501.

The first cam 503 includes the rotation shaft 503a and a protruding portion 503b, as illustrated in FIG. 22. Moreover, the first cam 503 includes a groove 503c into which the O-ring 506 is fitted, as illustrated in FIG. 23.

The wire 504 is connected to the operating portion 11 on the proximal end side and is movable in the insertion direction by operation of the operating portion 11. A distal end portion 504a of the wire 504 is connected to a wire connection portion 505b of the second cam 505, as illustrated in FIG. 22. Moreover, the wire 504 is connected to a lower portion in FIG. 23 with respect to the reference plane P (refer to FIGS. 22 and 23).

The second cam 505 includes a shaft hole 505a through which the rotation shaft 501a is inserted, and is rotatably supported with respect to the rotation shaft 501a. The second cam 505 includes the wire connection portion 505b, and includes a distal end side protruding portion 505c and a proximal end side protruding portion 505d, to be engaged with the protruding portion 503b of the first cam 503. The second cam 505 transmits the operation input from the wire 504 to the first cam 503.

Note that the first cam 503 and the second cam 505 function as an operation transmission mechanism for transmitting the operation input from the wire 504. The operation transmission mechanism converts the direction of transmitting the operation input from the wire 504 and transmits the operation such that the rotation shaft 503a rotates in a direction of elevating the treatment tool.

As illustrated in FIG. 23, the O-ring 506 is fitted in the groove 503c of the first cam 503 to maintain a portion between the distal end rigid portion 501 and the first cam 503 watertight. The cover 507 has a shape slightly larger than the opening of the distal end rigid portion 501 and is fixed to the distal end rigid portion 501 by adhesion, or the like. The O-ring 506 and the cover 507 maintain watertightness in a region including the wire 504 and the second cam 505 from the right side of the groove 503c of the first cam 503 in FIG. 23. As a result of this arrangement, these watertight regions are regions to which no dirt adheres at the use of the ultrasound endoscope, and thus, regions for which no cleaning is needed.

Next, the operation of rotating the treatment tool elevator base 502 of the ultrasound endoscope according to the fifth embodiment from the initial state to the elevated state will be described. First, when the wire 504 is pulled to the proximal end side by the operation of the operating portion 11 in the initial state of FIG. 22, the second cam 505 rotates clockwise in FIG. 22 around the rotation shaft 501a as an axis in conjunction with the wire 504. Furthermore, the proximal end side protruding portion 505d of the second cam 505 presses the protruding portion 503b of the first cam 503 to the right side in FIG. 22, whereby the first cam 503 rotates counterclockwise in FIG. 22 around the rotation shaft 503a as an axis. Rotation of the first cam 503 causes the treatment tool elevator base 502 fixed to the rotation shaft 503a of the first cam 503 to rotate integrally with the first cam 503, thereby turning the treatment tool elevator base 502 into the elevated state.

Figure 24:
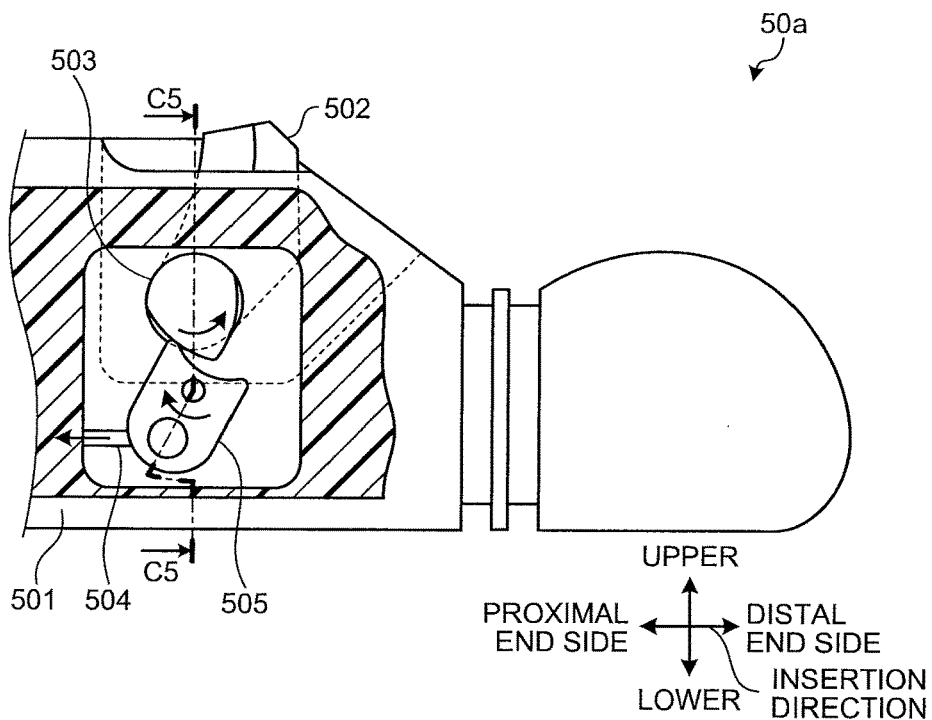
FIG. 24 is a diagram for illustrating an elevated state of the treatment tool elevator base.

FIG. 24 is a diagram for illustrating the elevated state of the treatment tool elevator base. When the wire 504 is pulled toward the proximal end side by the operation of the operating portion 11, each portion moves from the position of FIG. 22 in the direction of each of arrows in FIG. 24 in conjunction with the wire 504, thereby turning the treatment tool elevator base 502 into the elevated state illustrated in FIG. 24.

Moreover, in a case where the treatment tool elevator base 502 of the ultrasound endoscope is rotated from the elevated state to the initial state, it would be only required to press the wire 504 toward the distal end side. When the wire 504 is pressed to the distal end side, the second cam 505 is pressed to the right side in FIG. 24 in conjunction with the wire 504 and rotates counterclockwise in FIG. 24 around the rotation shaft 501a as an axis. Then, the distal end side protruding portion 505c of the second cam 505 presses the protruding portion 503b of the first cam 503 to the left side in FIG. 24, whereby the first cam 503 rotates clockwise in FIG. 24 around the rotation shaft 503a as an axis. Rotation of the first cam 503 causes the treatment tool elevator base 502 to rotate integrally with the first cam 503, thereby allowing the treatment tool elevator base 502 to return to the initial state.

Figure 25:
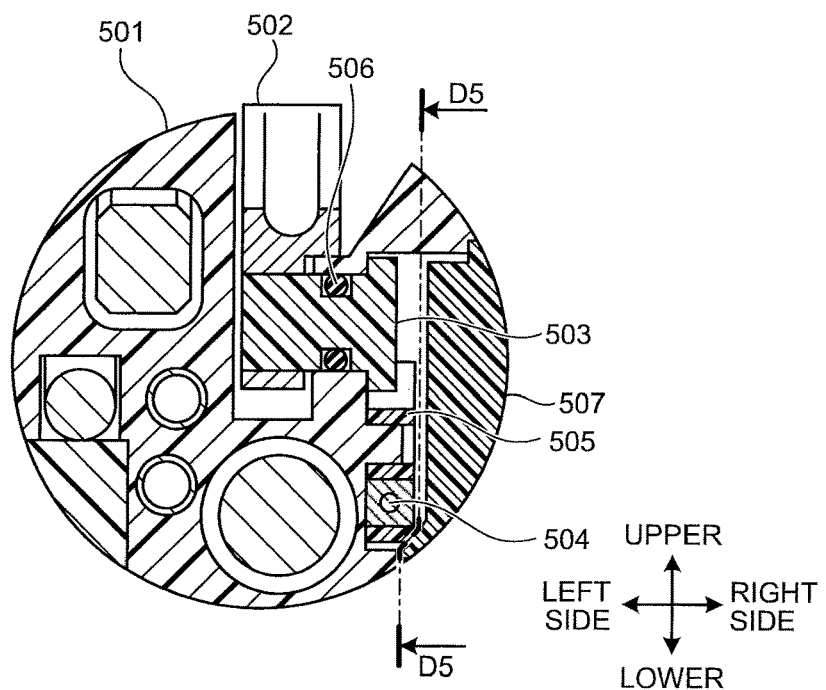
FIG. 25 is a cross-sectional view of the cross section taken along line C5-C5 in FIG. 24, viewed from the proximal end side.

FIG. 25 is a cross-sectional view of the cross section taken along line C5-C5 in FIG. 24 viewed from the proximal end side. FIG. 24 is a partial cross-sectional view of the cross section taken along line D5-D5 in FIG. 25, viewed from the right side. As illustrated in FIG. 25, watertightness of the portion between the first cam 503 and the distal end rigid portion 501 is maintained by the O-ring 506 even when the treatment tool elevator base 502 rotates from the initial state to the elevated state.

Note that, as illustrated in FIG. 23, the ultrasound endoscope according to the fifth embodiment has the gap G provided between a lower portion of the treatment tool elevator base 502 and the distal end rigid portion 501. The size of the gap G is the same as the case of the first embodiment. This arrangement enables cleaning by directly inserting a brush into this gap G during cleaning. That is, this ultrasound endoscope is an ultrasound endoscope having a good cleaning efficiency.

Moreover, in the ultrasound endoscope, since the opening 501b of the distal end rigid portion 501 has a tapered shape, the brush easily accesses the lower portion of the treatment tool elevator base 502 and around the rotation shaft 503a, leading to further enhancement in cleaning efficiency.

Moreover, in this ultrasound endoscope, the wire connection portion 505b is located at a portion lower than the reference plane P. Therefore, it is possible to provide the tapered shape in the opening 501b of the distal end rigid portion 501, and furthermore, with the presence of the gap G, it is also possible to suppress enlargement of the distal end of the insertion portion 10.

Furthermore, the ultrasound endoscope is configured to maintain the operational feeling of the user accustomed to the operation of conventional endoscopes, so as to suppress discomfort during operation. In this ultrasound endoscope, when the wire 504 is pulled toward the proximal end side, the treatment tool is elevated. Therefore, it is possible to elevate the treatment tool by the same operation as the conventional endoscope. This is because the operation transmission mechanism including the first cam 503 and the second cam 505 transmits operation such that the treatment tool is elevated when the wire 504 is pulled toward the proximal end side. As illustrated with the ultrasound endoscope, the operation transmission mechanism may include a cam. Moreover, the ultrasound endoscope has a long distance between the shaft hole 502a and the wire connection portion 505b and a long distance between the axis of the first cam 503 and the axis of the second cam 505, making it possible to reduce the force to be applied to the wire 504 in order to elevate the treatment tool. Therefore, user's operational feeling of the user is maintained with the ultrasound endoscope.

As described above, the ultrasound endoscope according to the fifth embodiment is an endoscope capable of enhancing cleaning efficiency without enlarging the distal end portion of the endoscope, and without deteriorating the user's operational feeling.

Sixth Embodiment

Figure 26:
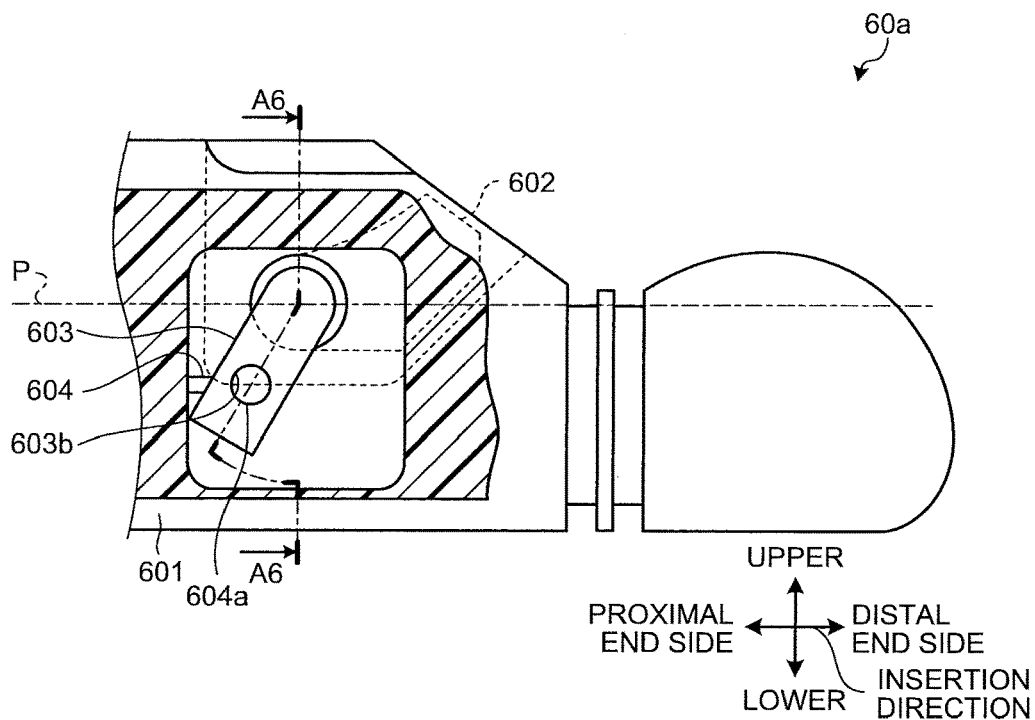
FIG. 26 is a schematic diagram illustrating a configuration of a main portion of an ultrasound diagnosis system including an ultrasound endoscope according to a sixth embodiment of the disclosure.
Figure 27:
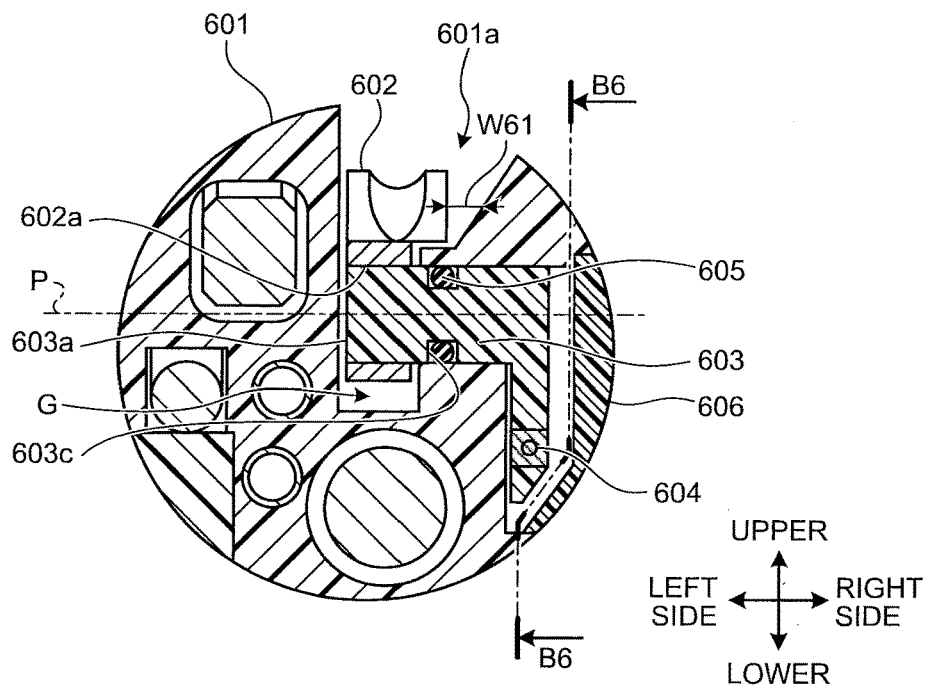
FIG. 27 is a cross-sectional view of the cross section taken along line A6-A6 in FIG. 26, viewed from the proximal end side.

Next, a sixth embodiment of the disclosure will be described. FIG. 26 is a schematic diagram illustrating a configuration of a main portion of an ultrasound diagnosis system including an ultrasound endoscope according to the sixth embodiment of the disclosure. FIG. 27 is a cross-sectional view taken along line A6-A6 in FIG. 26, viewed from the proximal end side. FIG. 26 is a partial cross-sectional view of a cross section taken along line B6-B6 in FIG. 27, viewed from the right side.

The ultrasound endoscope according to the sixth embodiment is the same as the ultrasound endoscope 2 according to the first embodiment except for a distal end portion 60a. Furthermore, since the treatment tool channel, the cable, or the like, of the ultrasound endoscope according to the sixth embodiment are also the same as the ultrasound endoscope 2 according to the first embodiment, the description of these components will be appropriately omitted.

As illustrated in FIG. 26, the distal end portion 60a includes a distal end rigid portion 601, a treatment tool elevator base 602, an arm 603, and a wire 604. The treatment tool elevator base 602 elevates the treatment tool. The arm 603 rotatably supports the treatment tool elevator base 602. The wire 604 transmits the operation input into the operating portion 11 to the insertion portion 10. Furthermore, as illustrated in FIG. 27, the distal end portion 60a includes an O-ring 605 and a cover 606. The O-ring 605 maintains a portion between the distal end rigid portion 601 and the arm 603 watertight. The cover 606 seals each of portions watertight.

As illustrated in FIG. 27, the distal end rigid portion 601 includes an opening 601a for accommodating the treatment tool elevator base 602 in the initial state. A cross section of the opening 601a, which is a cross section orthogonal to the insertion direction, has a tapered shape with a width W61 in the left-right direction in FIG. 27 increasing in the upper direction in FIG. 27.

A shaft hole 602a is formed in the treatment tool elevator base 602 as illustrated in FIG. 27. The treatment tool elevator base 602 is rotatably supported by the arm 603 by adhering a rotation shaft 603a of the arm 603 to the shaft hole 602a. Moreover, a gap G similar to that in the first embodiment is provided between the treatment tool elevator base 602 and the distal end rigid portion 601.

The arm 603 includes the rotation shaft 603a and a wire connection portion 603b as illustrated in FIG. 26. Moreover, the arm 603 includes a groove 603c into which the O-ring 605 is fitted, as illustrated in FIG. 27.

The wire 604 is connected to the operating portion 11 on the proximal end side and is movable in the insertion direction by operation of the operating portion 11. A distal end portion 604a of the wire 604 is connected to the wire connection portion 603b, as illustrated in FIG. 26. Moreover, the wire 604 is connected to a lower portion in FIG. 27 with respect to the reference plane P (refer to FIGS. 26 and 27).

As illustrated in FIG. 27, the O-ring 605 is fitted into the groove 603c of the arm 603 to maintain the portion between the distal end rigid portion 601 and the arm 603 watertight. The cover 606 has a shape slightly larger than the opening of the distal end rigid portion 601 and is fixed to the distal end rigid portion 601 by adhesion, or the like. The O-ring 605 and the cover 606 maintain watertightness in a region including the wire 604 from the right side of the groove 603c of the arm 603 in FIG. 27. As a result of this arrangement, these watertight regions are regions to which no dirt adheres at the use of the ultrasound endoscope, and thus, regions for which no cleaning is needed.

Next, the operation of rotating the treatment tool elevator base 602 of the ultrasound endoscope according to the sixth embodiment from the initial state to the elevated state will be described. In this ultrasound endoscope, the treatment tool is elevated by pressing the wire 604 toward the distal end side in FIG. 26. First, when the wire 604 is pressed to the distal end side by the operation of the operating portion 11 in the initial state of FIG. 26, the arm 603 rotates counterclockwise in FIG. 26 around the rotation shaft 603a as an axis in conjunction with the wire 604. Furthermore, rotation of the arm 603 causes the treatment tool elevator base 602 fixed to the rotation shaft 603a of the arm 603 to rotate integrally with the arm 603, thereby turning the treatment tool elevator base 602 into the elevated state.

Figure 28:
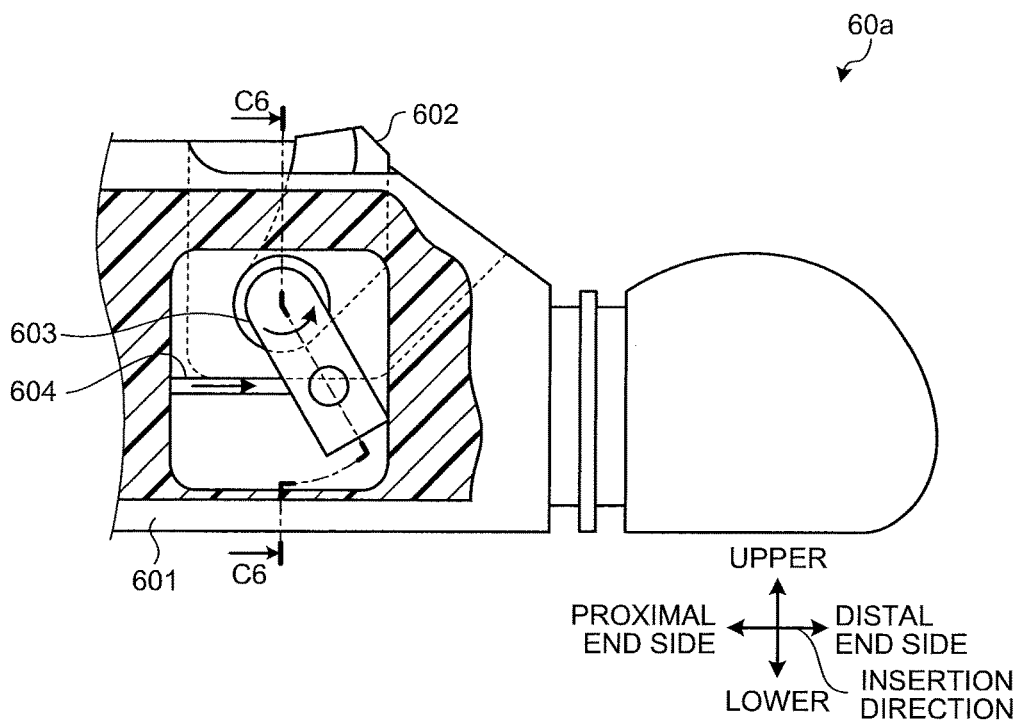
FIG. 28 is a diagram for illustrating an elevated state of the treatment tool elevator base.

FIG. 28 is a diagram for illustrating the elevated state of the treatment tool elevator base. When the wire 604 is pulled toward the proximal end side by the operation of the operating portion 11, each portion moves from the position of FIG. 27 in the direction of each of arrows in FIG. 28 in conjunction with the wire 604, thereby turning the treatment tool elevator base 602 into the elevated state illustrated in FIG. 28.

Moreover, in a case where the treatment tool elevator base 602 of the ultrasound endoscope is rotated from the elevated state to the initial state, it would be only required to press the wire 604 toward the proximal end side. When the wire 604 is pressed to the proximal end side, the arm 603 is pulled toward the left side in FIG. 28 in conjunction with the wire 604, and rotates clockwise in FIG. 28 around the rotation shaft 603a as an axis. When the arm 603 rotates, the treatment tool elevator base 602 rotates integrally with the arm 603, whereby the treatment tool elevator base 602 returns to the initial state.

Figure 29:
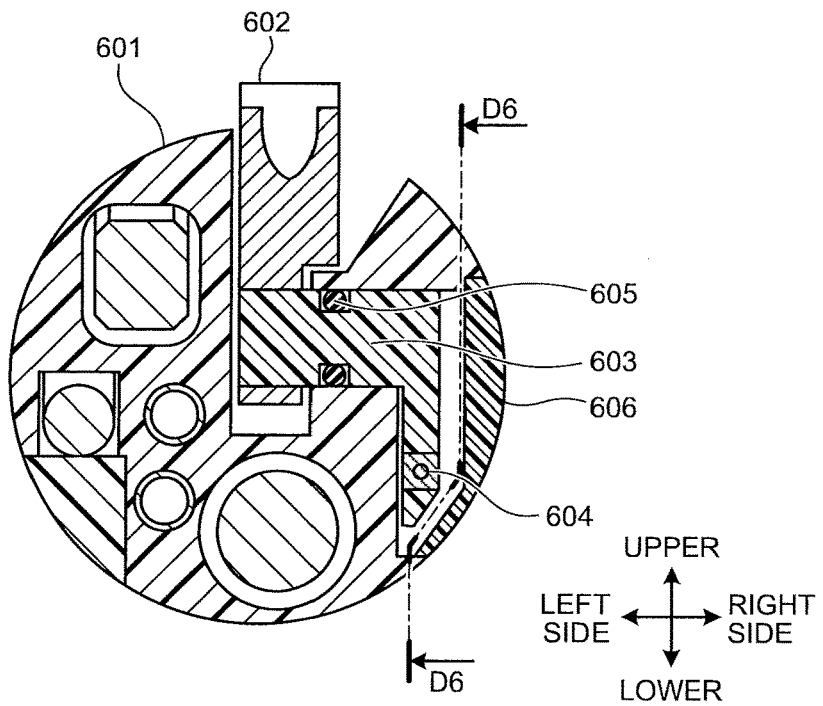
FIG. 29 is a cross-sectional view of the cross section taken along line C6-C6 in FIG. 28, viewed from the proximal end side.

FIG. 29 is a cross-sectional view of the cross section taken along line C6-C6 in FIG. 28, viewed from the proximal end side. FIG. 28 is a partial cross-sectional view of the cross section taken along line D6-D6 in FIG. 29, viewed from the right side. As illustrated in FIG. 29, watertightness of the portion between the arm 603 and the distal end rigid portion 601 is maintained by the O-ring 605 even when the treatment tool elevator base 602 rotates from the initial state to the elevated state.

Note that, as illustrated in FIG. 27, the ultrasound endoscope according to the sixth embodiment has the gap G provided between a lower portion of the treatment tool elevator base 602 and the distal end rigid portion 601. The size of the gap G is the same as the case of the first embodiment. This arrangement enables cleaning by directly inserting a brush into this gap G during cleaning. That is, this ultrasound endoscope is an ultrasound endoscope having a good cleaning efficiency.

Moreover, in the ultrasound endoscope, since the opening 601a of the distal end rigid portion 601 has a tapered shape, the brush easily accesses the lower portion of the treatment tool elevator base 602 and around the rotation shaft 603a, leading to further enhancement in cleaning efficiency.

Moreover, in this ultrasound endoscope, the wire connection portion 603b is located at a portion lower than the reference plane P. Therefore, it is possible to provide the tapered shape in the opening 601a of the distal end rigid portion 601, and furthermore, with the presence of the gap G, it is also possible to suppress enlargement of the distal end of the insertion portion 10.

Furthermore, the ultrasound endoscope is configured to maintain the operational feeling of the user accustomed to the operation of conventional endoscopes, so as to suppress discomfort during operation. The ultrasound endoscope has a long distance between the shaft hole 602a and the wire connection portion 603b, making it possible to reduce the force applied to the wire 604 in order to elevate the treatment tool. Therefore, user's operational feeling of the user is maintained with the ultrasound endoscope.

Moreover, while the ultrasound endoscope is configured such that the treatment tool is elevated when the wire 604 is pressed to the distal end side, it is possible to configure such that the treatment tool is elevated when the wire 604 is pulled toward the proximal end side by arranging the operation transmission mechanism on the operating portion 11 side.

Figure 30:
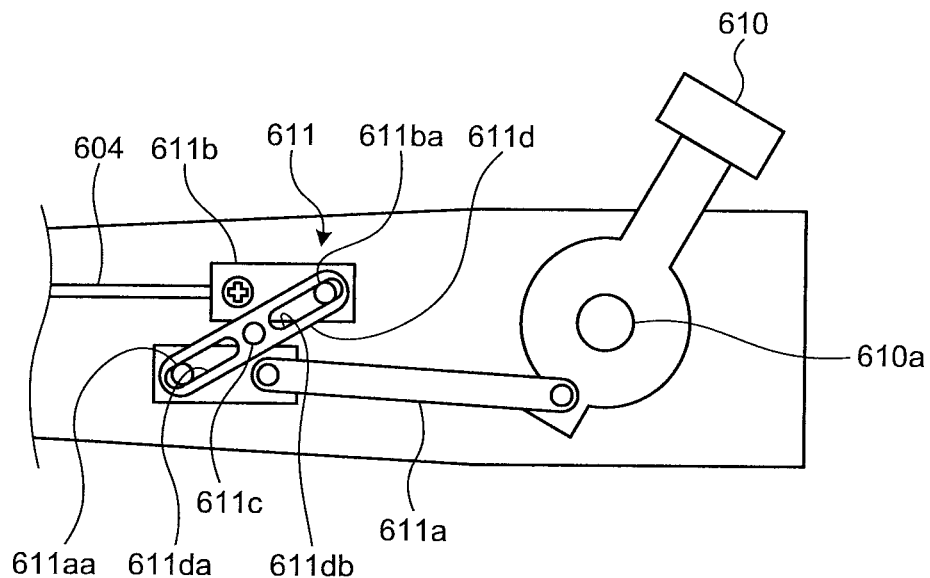
FIG. 30 is a diagram for illustrating operation of an operation transmission mechanism arranged on an operating portion side.

FIG. 30 is a diagram for illustrating the operation of the operation transmission mechanism arranged on the operating portion side. As illustrated in FIG. 30, an operation transmission mechanism 611 is connected to an operation lever 610 and includes a connection portion 611a, a connection portion 611b, a rotation shaft 611c, and a rotating member 611d. The connection portion 611a is connected to the operation lever 610. The connection portion 611b is connected to the wire 604 extending to the distal end portion 60a. The rotating member 611d is rotatably supported by the rotation shaft 611c.

The operation lever 610 is rotatably supported by a rotation shaft 610a. The connection portion 611a includes an engagement portion 611aa, while the connection portion 611b includes an engagement portion 611ba. The rotating member 611d includes a long hole 611da and a long hole 611db. Then, the engagement portion 611aa of the connection portion 611a is engaged with the long hole 611da of the rotating member 611d, while the engagement portion 611ba of the connection portion 611b is engaged with the long hole 611db of the rotating member 611d.

Next, the operation of the operation transmission mechanism 611 will be described. First, when the operation lever 610 is operated to the left side in FIG. 30 in the initial state illustrated in FIG. 30, the operation lever 610 rotates counterclockwise in FIG. 30 around the rotation shaft 610a as a rotation shaft. When the operation lever 610 rotates, the connection portion 611a connected to the operation lever 610 is pulled to the right side in FIG. 30. Then, the engagement portion 611aa of the connection portion 611a comes into engagement with the long hole 611da of the rotating member 611d, whereby the rotating member 611d rotates counterclockwise in FIG. 30. Rotation of the rotating member 611d causes the engagement portion 611ba of the connection portion 611b to be engaged with the long hole 611db of the rotating member 611d, thereby pressing the connection portion 611b to the left side in FIG. 30. Then, the wire 604 connected to the connection portion 611b is pressed to the left side in FIG. 30.

Figure 31:
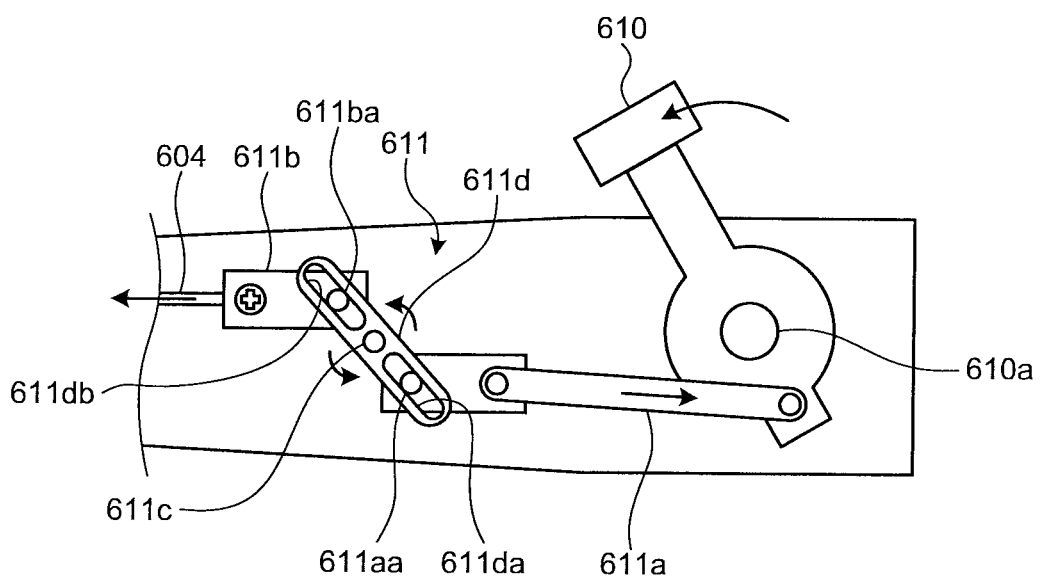
FIG. 31 is a diagram for illustrating an elevated stated of the operation transmission mechanism arranged on the operating portion side.

FIG. 31 is a diagram for illustrating the elevated state of the operation transmission mechanism arranged on the operating portion side. That is, FIG. 31 is a diagram illustrating a state after operating the operation lever 610. By operating the operation lever 610, each of the members operates in conjunction with the direction of each of arrows in FIG. 31, thereby pressing the wire 604 to the distal end side.

In other words, the operation transmission mechanism 611 converts the operation transmission direction from the direction toward the right side in FIG. 30 to the direction toward the left side in FIG. 30. As a result, the treatment tool is elevated in a case where the operation in the direction toward the proximal end side is input into the operating portion 11. Therefore, it is possible to perform operation similar to the operation of conventional endoscopes, and the user's operational feeling is maintained. In this manner, the operation transmission mechanism may be either arranged on the side of the operating portion 11, or arranged at the distal end portion as in the other embodiments.

As described above, the ultrasound endoscope according to the sixth embodiment is an endoscope capable of enhancing cleaning efficiency without enlarging the distal end portion of the endoscope, and without deteriorating the user's operational feeling.

According to some embodiments, it is possible to realize an endoscope capable of enhancing the cleaning efficiency without enlarging the distal end portion of the endoscope and without deteriorating user's operational feeling.

Further effects and variations can be easily derived by those skilled in the art. Thus, the broader aspects of the present invention are not limited to the specific details and representative embodiments illustrated and described as such. For example, the operation transmission mechanism can be configured by appropriately combining the gear, the cam, the link, and the arm, etc. described in the above embodiments. Accordingly, various modifications are possible without departing from the spirit or scope of the general inventive concept as defined by the appended claims and their equivalents.

What is claimed is:

1. An endoscope comprising an insertion portion to be inserted into a subject, the endoscope being configured to allow a treatment tool to protrude from a distal end of the insertion portion, the endoscope further comprising:

a treatment tool elevator base configured to be supported by a rotation shaft arranged at a distal end portion of the insertion portion, the treatment tool elevator base being configured to be elevated by rotation around the rotation shaft with respect to a direction in which the insertion portion extends;

an operating portion configured to be arranged on a proximal end side of the insertion portion, the operating portion being configured to input an operation of changing an angle of elevating the treatment tool with respect to the treatment tool elevator base;

a wire configured to be connected to the operating portion, the wire being configured to be arranged along the direction in which the insertion portion extends;

a first member including a first engagement portion, the first engagement portion being formed integrally with the rotation shaft; and a second member including a second engagement portion configured to be engaged with the first engagement portion of the first member and a wire connection portion to be connected to the wire, the second member being configured to be rotatably supported with respect to the rotation shaft and to transmit the operation to the treatment tool elevator base, wherein the wire connection portion is positioned on a side opposite to an elevation side on which the treatment tool is elevated with respect to a reference plane including the direction in which the insertion portion extends and a direction along an axis of the rotation shaft, the endoscope further comprising a distal end rigid portion arranged at the distal end of the insertion portion and comprising the distal end portion of the insertion portion, wherein the distal end rigid portion includes an opening for accommodating the treatment tool elevator base in an initial state that is a state before elevating the treatment tool, and a cross section of the opening, which is a cross section orthogonal to the direction in which the insertion portion extends, is formed in a tapered shape with an opening width of the opening increasing in a direction of elevating the treatment tool.

2. An endoscope according to claim 1, comprising an insertion portion to be inserted into a subject, the endoscope being configured to allow a treatment tool to protrude from a distal end of the insertion portion, the endoscope further comprising:

a treatment tool elevator base configured to be supported by a rotation shaft arranged at a distal end portion of the insertion portion, the treatment tool elevator base being configured to be elevated by rotation around the rotation shaft with respect to a direction in which the insertion portion extends;

an operating portion configured to be arranged on a proximal end side of the insertion portion, the operating portion being configured to input an operation of changing an angle of elevating the treatment tool with respect to the treatment tool elevator base;

a wire configured to be connected to the operating portion, the wire being configured to be arranged along the direction in which the insertion portion extends;

a first member including a first engagement portion, the first engagement portion being formed integrally with the rotation shaft; and a second member including a second engagement portion configured to be engaged with the first engagement portion of the first member and a wire connection portion to be connected to the wire, the second member being configured to be rotatably supported with respect to the rotation shaft and to transmit the operation to the treatment tool elevator base, wherein the rotation shaft includes: a first rotation shaft; and a second rotation shaft that is a shaft different from the first rotation shaft, the treatment tool elevator base is supported by the first rotation shaft arranged at the distal end portion of the insertion portion and configured to be elevated by rotation around the first rotation shaft with respect to a direction in which the insertion portion extends, the first member is formed integrally with the first rotation shaft, the second member is configured to be rotatably supported with respect to the second rotation shaft, and the wire connection portion is positioned on a side opposite to an elevation side on which the treatment tool is elevated with respect to a reference plane including the direction in which the insertion portion extends and a direction along an axis of the first rotation shaft.

3. The endoscope according to claim 2, wherein the treatment tool is elevated when the operation of pulling the wire connection portion of the second member with the wire toward the proximal end side is input into the operating portion, the connection portion being connected to the operating portion via the wire.

4. The endoscope according to claim 3, further comprising an operation transmission mechanism including the first member and the second member, the operation transmission mechanism being configured to transmit the operation input from the wire where that the first rotation shaft rotates in a direction of elevating the treatment tool.

5. The endoscope according to claim 2, wherein the second member is arranged in a region in which water tightness is maintained.

6. The endoscope according to claim 2, further comprising an ultrasound transducer configured to be arranged at the distal end of the insertion portion and configured to transmit ultrasound and receive ultrasound reflected on an examination target, wherein a cable connected to the ultrasound transducer is arranged, on the side opposite to the elevation side on which the treatment tool is elevated with respect to the reference plane, along the direction in which the insertion portion extends.

* * * * *